United States Patent [19]

Milich et al.

[11] Patent Number: 4,683,136

[45] Date of Patent: Jul. 28, 1987

[54] PROTEINACEOUS ANTIGENS WITH CONFORMATION-INDEPENDENT AND CONFORMATION-DEPENDENT DETERMINANTS

[75] Inventors: David Milich, Mira Mesa; Frank Chisari, Del Mar, both of Calif.

[73] Assignee: Scripps Clinic and Research Foundation, La Jolla, Calif.

[21] Appl. No.: 708,746

[22] Filed: Mar. 6, 1985

[51] Int. Cl.$^4$ .............................................. A61K 39/12
[52] U.S. Cl. ........................................ 424/89; 435/5; 435/184; 435/948; 435/7; 436/86; 436/543; 436/820; 436/518; 530/402; 530/403; 530/826
[58] Field of Search ............... 260/112 R; 435/5, 184, 435/948, 7; 436/86, 518, 543, 820; 424/89; 530/402, 403, 826

[56] References Cited

PUBLICATIONS

Lerner, R. A., Nature, vol. 299, (1982), pp. 592–596.
Neurath, et al., Science, vol. 224, (1984), pp. 392–395.
Lerner et al., Proc. Natl. Acad. Sci. USA, vol. 78, No. 6, (1981), pp. 3403–3407.
Gerin, et al., Proc. Natl. Acad. Sci. USA, vol. 80, No. 1, (1983), pp. 2365–2369.
Dienstag et al., Ann. Intern. Med., 101, 34–40 (1984).
Francis et al, Ann. Intern. Med., 97, 362–366 (1982).
Szmuness et al., Hepatology, 1, 377–385 (1981).
Szumness et al, N. Engl. J. Med., 303, 833–841 (1980).
Bittle et al, Nature, 298 30 (1982).
Valenzuela, Nature, 280, 815 (1979).
Pasek et al, Nature, 282, 575 (1979).
Charney et al., Nucleic Acid Res., 7, 335 (1979).
Tiollais et al, Science, 213 406 (1980).
Green et al., Cell, 28, 477 (1982).

Primary Examiner—Christine M. Nucker
Assistant Examiner—Stephen C. Wieder
Attorney, Agent, or Firm—Dressler, Goldsmith, Shore, Sutker & Milnamow, Ltd.

[57] ABSTRACT

A single polypeptide antigen that includes the amino acid residue sequence and epitope of a conformation-independent antigenic determinant and the amino acid residue sequence but lacks the epitope of a conformation-dependent antigenic determinant is disclosed as are methods of its manufacture and use and articles of manufacture using the same. The uses of the pre-S(2) region polypeptide encoded by the hepatitis B virus genome as a T cell proliferating agent and as a potentiator for enhancing the humoral immune response of animals that exhibit a low humoral response to an S region-containing immunogen are also disclosed.

8 Claims, 9 Drawing Figures

PROTEINACEOUS ANTIGENS WITH CONFORMATION-INDEPENDENT AND CONFORMATION-DEPENDENT DETERMINANTS

DESCRIPTION

TECHNICAL FIELD

The present invention relates to antibody-antigen interactions, and particularly to interactions involving proteinaceous antigens that contain conformation-independent and conformation-dependent determinants.

BACKGROUND ART

A single proteinaceous antigen may contain a number of antigenic determinants that each include a number of specific epitopes that immunoreact with and are bound by antibodies directed or raised to the antigen as immunogen. Thus, the genome of a cell such as a pathogen may encode several antigenic determinants and epitopes that are recognized by a mammalian immune system as being foreign and that induce production of antibodies.

Where the antigenic determinants are part of a pathogen, antibody binding to particular epitopes may be of clinical importance in that such binding may lead to protection of the host animal in which the antibodies were raised. On the other hand, antibody binding to other epitopes may be of lesser importance to protection from the pathogen, but may provide information as to the strain of the immunizing pathogen or the stage of the disease state induced by the pathogen. It can therefore be seen that it may be clinically important or of scientific interest to be able to distinguish antibodies that immunoreact with and bind to one epitope of a given antigen from antibodies that immunoreact with and bind to one or more other epitopes of the same proteinaceous antigen Early work with globular proteins seemed to indicate that antigenic determinants of those proteins were generally conformation-dependent; i.e., the epitopes were determined by both the amino acid residue sequence of the region and by the region's three-dimensional structure. For example, work reported by Arnon et al., *Proc. Natl. Acad. Sci. USA*, 62, 163 (1968) indicated that the so-called "loop" of the non-pathogenic, endogenous protein egg white lysosyme was a conformation-dependent antigenic determinant.

More recently, however, work by R. A. Lerner and co-workers using polypeptide immunogens whose sequences correspond to antigenic determinants of pathogen-related proteins has indicated that protection of a host animal from a pathogen may be obtained by use of vaccines containing immunogenic linear polypeptides that may assume many conformations. [See for example, Bittle et al., *Nature*, 298, 30 (1982); and Gerin et al., *Proc. Natl. Acad. Sci. USA*, 80, 2365 (1983).]The work of Lerner and co-workers thus appears to imply that a strict requirement of conformation-dependence of polypeptide immunogens, and therefore the existence of only conformation-dependent antigenic determinants and epitopes, is an incorrect assumption.

The heptatitis B virus (HBV) is associated worldwide with both acute and chronic diseases in man. A recent report has directly implicated that virus with hepatocellular carcinoma [Moriarty et al., *Science*, 227, 429 (1985); and Beasley et al., *Lancet*, 1129, Nov. 21, 1981.]

Immunologic markers encoded by the genome of HBV include the surface antigen (HBsAg), the core antigen (HBcAg), the core-derived HBeAg, and the so-called HBxAg reported on by Moriarty et al., above. Since HBsAg-specific antibodies are protective against HBV infection, virus-free HBsAg-containing envelopes present in the plasma of chronic carriers have served as a source of HBV vaccines.

The HBsAg is composed of a major polypeptide denominated p25, and its glycosylated form denominated Gp28. [peterson et al., *Proc. Natl. Acad. Sci. USA*, 74 1540 (1977).]The complete 226 amino acid sequence of the P25 polypeptide of HBsAg has been deduced from partial amino acid sequence data and from the neucleotide sequence of the viral gene (S) that encodes this polypeptide. [Valenzuela, *Nature*, 280, 815 (1979); Pasek et al., *Nature*, 282, 575 (1979); and Charnay et al., *Nucleic Acids Res.*, 7, 335 (1979).]

Historically, additional higher molecular weight polypeptides associated with HBsAg were considered aggregates of P25 and GP28. However, P25 begins at the third possible translational initiation site of a larger open reading frame (ORF), and is preceded in phase by 163 or 174 condons (subtype-dependent) designated as the pre-S region. Tiollais et al., *Science*, 213, 406 (1980).

An HBV-associated 33–36 kilodalton (kD) glycoprotein (GP33) has been reported by Stibbe and Gerlich, *J. Virol*, 46, 626 (1983), and it was suggested that the sequence of GP33 starts at the second translational initiation signal of the ORF, which is 55 codons upstream of the third translation signal. [Cattaneo et al., *Nature (London)*, 305, 336 (1983).]It has also been reported that GP33 consists of the P25 sequence and an amino-terminal 55 amino acid residues encoded in what is now called the pre-S(2) region [Stibbe and Gerlich, above; and Machida et al., *Gastorenterol.*, 86, 910 (1984).]

In support of that report, Neurath et al. *Science*, 224, 392 (1984) reported synthesis of a peptide encompassing the 26 amino-terminal amino acid residues of the pre-S(2) region. They reported that anti-peptide antibodies reacted with GP33. Recently, the products encoded from the first translational initiation site have been identified as P39/GP42, consisting of the GP33 sequence and the amino-terminal 108–119 amino acid residues encoded by the genome in the pre-S(1) region [Heermann et al., *J. Virol.*, 52, 396 (1984).]

The fact that the pre-S region is conserved in all the described HBV DNA sequences and through evolution [Laub et al., *J. Virol.*, 48, 271 (1983)]suggests a functional role for this region. This interpretation is enhanced by the observation that both the Gp42 and Gp33 polypeptides appear to be preferentially expressed in viremic carriers as opposed to carriers with minimal or no infectious virions in the blood. [Stibbe and Gerlich; and Heermann et al., above.]This suggests a correlation between viral replication and synthesis of the higher molecular weight polypeptides of HBsAg.

Additionally, the receptor for polymerized human albumin, which has been suggested to mediate viral attachment, has been reported to be localized on GP33. [Machida et al., *Gastroenterol.*, 85, 320 (1982).]The implications of these recent findings relative to HBV vaccine development and mechanisms of immune-mediated viral clearance are apparent, and have prompted an investigation of the immune response to the S- and pre-S(2)-encoded GP33 polypeptide of HBsAg that is discussed hereinafter.

BRIEF SUMMARY OF THE INVENTION

The present invention contemplates a polypeptide conformation-independent antigen that is a single molecule encoded by the genome that encodes a proteinaceous antigen that includes a conformation-dependent antigenic determinant and at least one conformation-independent antigenic determinant.

The polypeptide antigen is prepared by providing a single proteinaceous antigen molecule that includes the amino acid residue sequence and epitope of a conformation-dependent antigenic determinant and the amino acid residue sequence and epitope of a conformation-independent antigenic determinant. An effective amount of a denaturing agent such as a mixture of a surfactant and a cystine disulfide bond-breaking (reducing) agent is admixed in an aqeuous medium with the proteinaceous antigen. The admixture is maintained for a predetermined time sufficient for the denaturing agent to substantially denature the conformation-dependent antigenic determinant, and form a polypeptide antigen that contains (i) the amino acid residue sequence and epitope of a conformation-independent antigenic determinant, and (ii) the amino acid residue sequence but lacks the epitope of a conformation-dependent antigen. The polypeptide antigen so prepared is then recovered.

In a preferred embodiment, the proteinaceous antigen is an HBsAg particle containing the 34 kD polypeptide such as the HBsAg/P34 particle produced by hepatitis B virus pre-S(2) and S region genome-transfected into Chinese hamster ovary cells. The conformation-independent determinant of that antigen is the pre-S(2) region, while the conformation-dependent determinant is the S region.

A diagnostic system for a solid phase immunological assay of a sample for the presence of antibodies directed to a conformation-independent antigenic determinant or for an antigen that contains the epitope of the conformation-independent determinant constitutes another aspect of this invention. A diagnostic system of this invention comprises at least one container that includes, bound to a solid matrix as a solid support, an effective amount of a polypeptide antigen comprising (i) the amino acid residue sequence of a conformation-dependent antigenic determinant but lacking the epitope of that determinant (and is therefore not bound by antibodies directed to that determinant) and (ii) the amino acid residue sequence and epitope of a conformation-independent antigenic detererminant (and is therefore bound by antibodies directed to that determinant).

A diagnostic system used to detect antibodies preferably includes a second container that includes an effective amount of an indicating means capable of signalling the immunoreaction of antibodies from a sample to be assayed with the conformation-independent determinant. A diagnostic system used to detect the antigen preferably includes a second container that includes a predetermined amount of known antibodies that immunoreact with and bind to the epitope assayed for and an epitope of the conformation-independent determinant, and also a third container that includes indicating means similar to those described above.

Solid phase assay methods are also contemplated. One method detects the presence of antibodies directed to a conformation-independent antigen, preferably in the presence of antibodies directed to a conformation-dependent antigen, in a sample to be assayed, and comprises the following steps: A solid support that comprises an effective amount of a polypeptide antigen affixed to a solid matrix is provided. The affixed polypeptide molecule contains (i) the amino acid residue sequence and epitope of a conformation-independent antigenic determinant, and (ii) the amino acid residue sequence of a conformation-dependent antigenic determinant but lacks the epitope of that antigenic determinant. The solid support and an aliquot of a liquid sample to be assayed for antibodies directed to the conformation-independent antigenic determinant are admixed to from a solid/liquid phase admixture. That admixture is maintained for a predetermined period of time sufficient for antibodies directed to the conformation-independent antigenic determinant to immunoreact with and bind to the conformation-independent antigenic determinant of the solid support. The solid and liquid phases are then separated, and the presence of antibodies bound to the solid support are thereafter determined. That determination is typically performed by the use of an indicating means that signals the presence of antibodies bound to the solid support.

Another method detects the presence of an antigenic epitope in a sample to be assayed. That epitope immunoreacts with and is bound by antibodies that immunoreact with and bind to an epitope of a conformation-independent antigenic determinant. This method includes the following steps: A solid support such as that provided in the above assay is provided. An aliquot of a liquid sample to be assayed is admixed with a predetermined amount of known antibodies that immunoreact with and bind to the assayed antigenic epitope as well as with and to an epitope of the conformation-independent determinant to form a liquid phase admixture. The liquid admixture is maintained for a predetermined period of time sufficient for the known antibodies to immunoreact with and bind to antigenic epitope assayed. The liquid phase admixture is thereafter admixed with the solid phase to form a solid/liquid phase admixture. That admixture is maintained for a period of time sufficient for the known antibodies to immunoreact with and bind to an epitope of the antigenic determinant of the solid support. The solid/liquid phase admixture is then separated, and the presence of antibodies bound to the solid support is determined. A difference between the amount of bound antibodies determined and a control amount of the known antibodies bound in the absence of an assayed sample indicates the presence of the antigenic epitope in the assayed sample.

BRIEF DESCRIPTION OF THE DRAWINGS

In the Figures forming a part of this disclosure.

The IgG antibody responses specific for the S region (●; assayed on HBsAg/P25) and the S plus pre-S(2)

region (0; assayed on HBsAg/P34) were determined by solid-phase radioimmune assay (RIA) at 10 and 24 days following primary immunization and 2 weeks following secondary immunization (2°) with one-half the amount of immunogen in incomplete Freund's adjuvant (IFA) using the methods reported by Milich and Chisari, *J. Immunol.*, 129, 320 (1982), as discussed in detail hereinafter. For comparison, the broken line (■) represents the response of mice immunized i.p. with 4 ug of HBsAg/P25 in CFA. Anti-HBs titers are expressed as the highest dilution to yield 2.5 times the counts of preimmunization sera.

Figure 1:
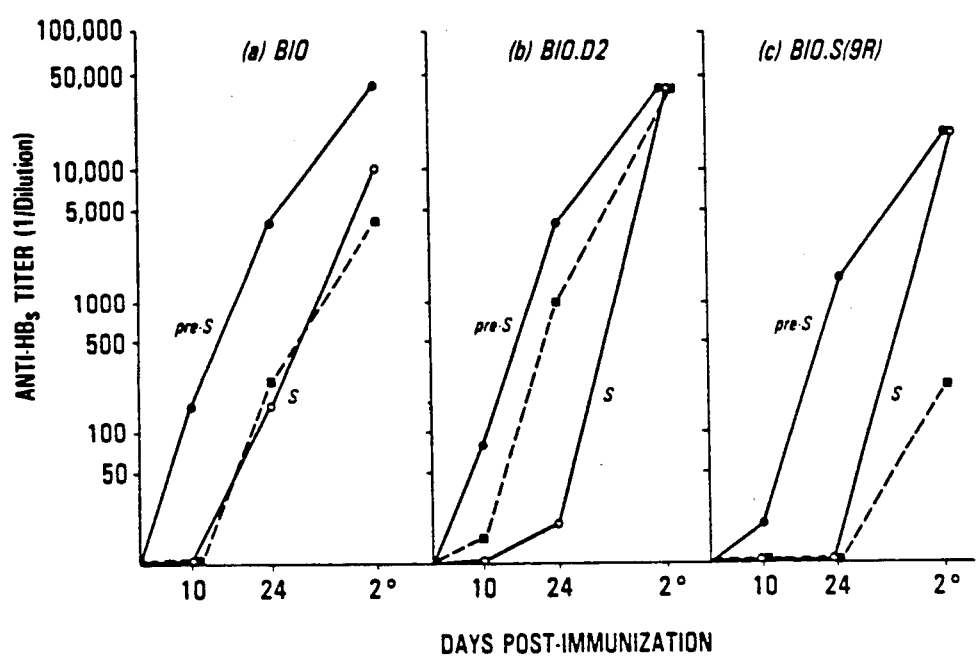
FIG. 1 contains three graphs that illustrate comparative anti-S and anti-pre-S(2) in vivo antibody production. Groups of 5 mice of the indicated BlO, BlO.D2 and BlO.S(9R) strains were immunized intraperitonally (i.p.) with 1 microgram (ug) of HBsAg/P34 in complete Freund's adjuvant (CFA) obtained from transfected Chinese hamster ovary (CHO) cells. The relative amount of P34 in the CHO-derived HBsAg particles was 35% of which the pre-S(2) region accounts for approximately 25 percent by weight of P34 [Michel et al., *Proc. Natl. Acad. Sci. U.S.A.*, 81, 7708 (1985)]. Therefore, a one ug dose of HBsAg/P34 is equivalent to 0.913 ug of S region protein and 0.087 ug of pre-S(2) region protein.
Figure 2:
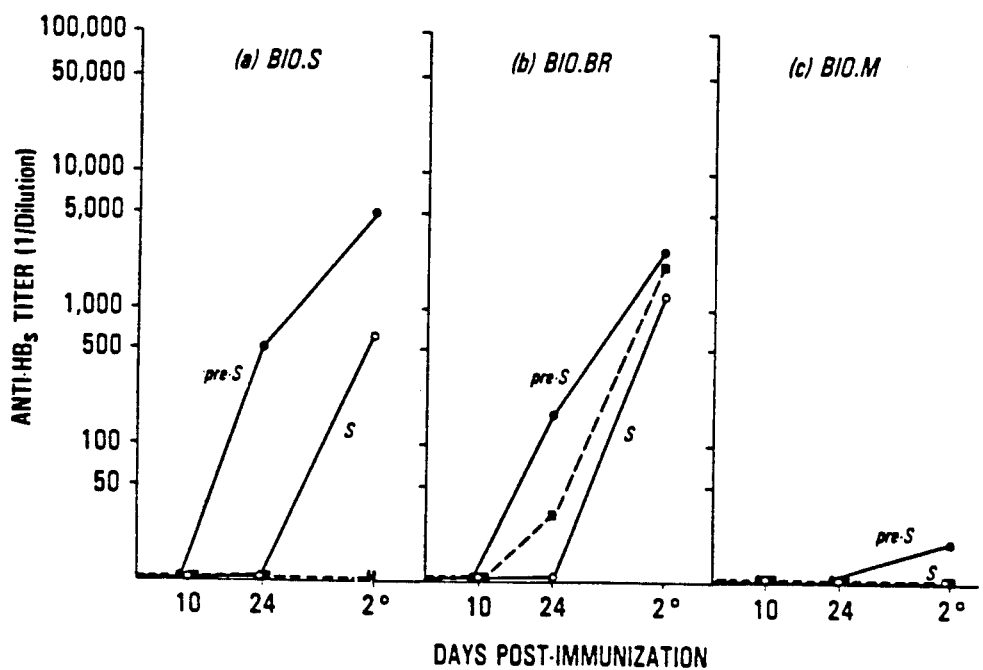

FIG. 2 contains three further graphs further illustrating comparative anti-S and anti-pre-S(2) region in vivo antibody production for mouse strains B10.S, B10.BR and B10.M. Groups of 5 mice of the indicated strains were immunized and sera were analyzed as described in FIG. 1.

Figure 3:
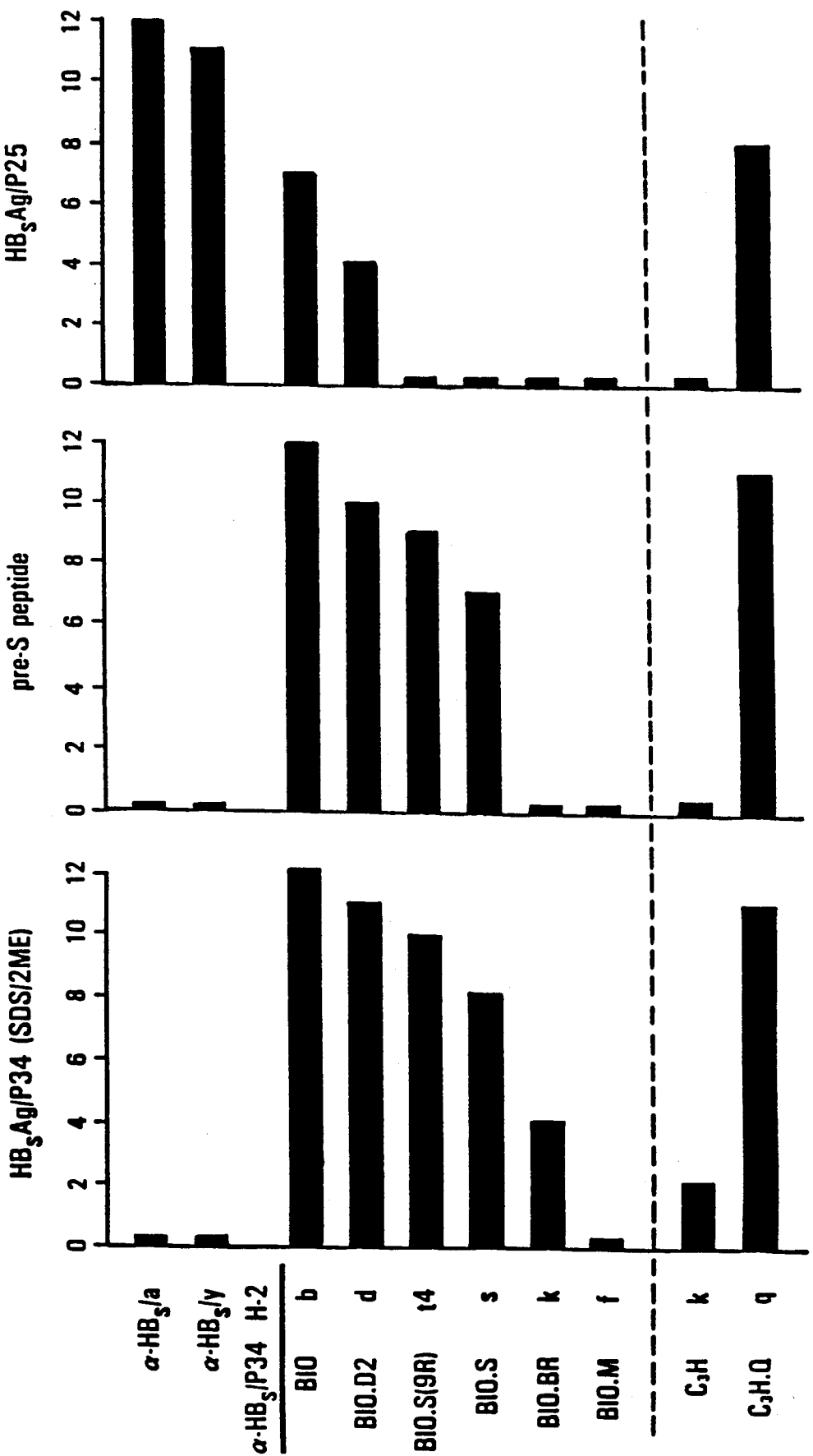

FIG. 3 contains three bar graphs that illustrate the specificity and H-2 restriction of the anti-pre-S(2) antibody response. H-2 Congenic, murine strains were immunized with 1 ug of HBsAg/P34 in CFA, and 24-day post imunization sera were analyzed by RIA for IgG antibody specific for the pre-S(2) region of HBsAg/P34, pre-S(2) peptide and HBsAg/P25.

The pre-S(2) region-specific RIA of this invention was developed utilizing solid-phase reduced and denatured HBsAg/P34 particles [HBsAg/P34(SDS/2ME)]. Briefly, HBsAg/P34 was treated with a mixture that contained a final concentration of 2 percent sodium dodecyl sulfate (SDS), and 2 percent 2-mercaptoethanol (2ME) for a time period of 2 hours at 37° C., diluted in 0.1M, pH 9.6 bicarbonate buffer, coated overnight on microtiter plates, and used in the standard RIA assay reported by Milich and Chisari, *J. Immunol*, 129, 130 (1982). This treatment was shown to reduce S region antigenicity by greater than 90%, and did not affect pre-S(2) region antigenicity.

The reactivities of group (anti-HBs/a) and subtype-specific (anti-HBs/y) antisera raised against HBsAg/P25 are also shown. Anti-HBs titers are expressed as the reciprocal of the $\log_2$ of the highest dilution to yield 2.5 times the counts of preimmunization sera. The H-2 haplotype of each strain is shown.

Figure 4:
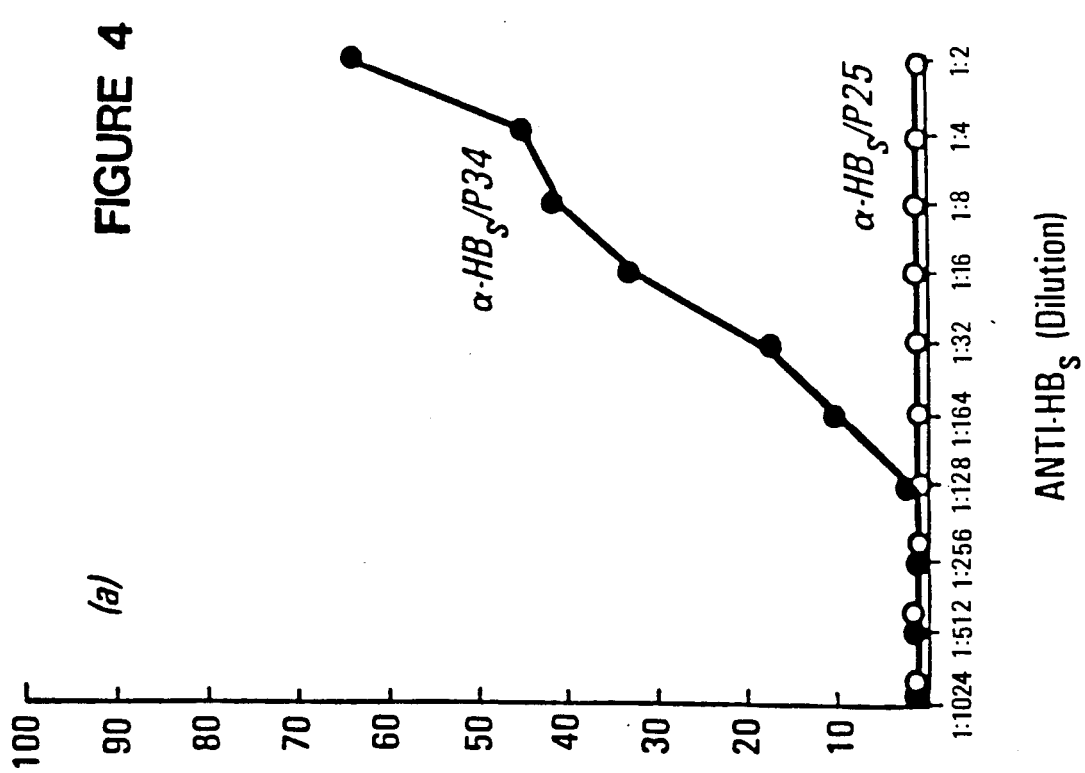

FIG. 4 contains two graphs that illustrate competitive antibody inhibition assays comparing anti-native pre-S(2) and anti-pre-S(2) peptide antisera. In graph (a), solid phase-affixed HBsAg/P34 was admixed and maintained (preincubated) with dilutions of mouse anti-native pre-S(2) directed-antibodies (●) for about 18 hours (overnight) at 4° C. limiting amount (1:5000) of rabbit anti-pre-S(2) peptide-directed antibodies was added followed by $^{125}$I-labelled anti-rabbit IgG, and the degree of inhibition was determined. Antibodies directed to HBsAg/P25 (0) were used as a control. In graph (b), solid phase-affixed HBsAg/P34 was preincubated with dilutions of rabbit anti-pre-S(2) peptide-directed antibodies (●) for about 18 hours (overnight) at 4° C. A limiting amount (1:500) of mouse anti-native pre-S(2) was added followed by $^{125}$I-labelled anti-mouse IgG, and the degree of inhibition was determined. Antibodies directed to an S region synthetic peptide (0) were used as a control.

Figure 5:
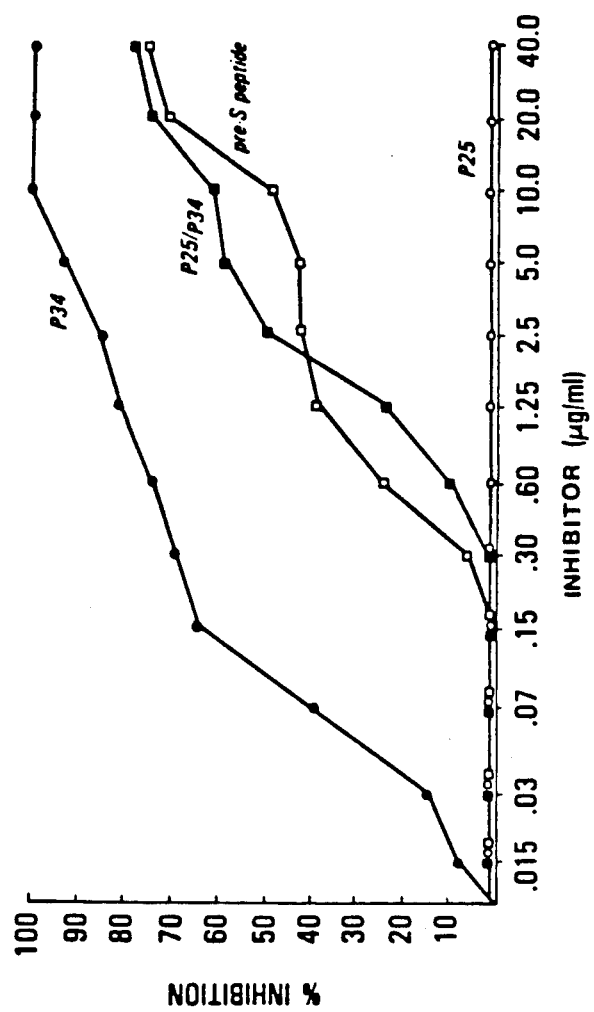

FIG. 5 is a graph that illustrates detection of encoded pre-S(2) region determinants on HBsAg particles and the pre-S(2) synthetic peptide. Varying concentrations of HBsAg/P34(●), HBsAg/P25(0), HBsAg/P25/P34 (■; a serum-derived:HBsAg with a trace amount of GP 34) and the synthetic pre-S(2) peptide (□) as inhibiting antigens were preincubated for about 18 hours (overnight) with a constant dilution (1:500) of mouse (B10) anti-pre-S(2) antisera. The antibody-antigen mixtures were then added to solid-phase HBsAg/P34 (0.lug/well), and the degree of inhibition was determined for each immunoreaction.

Figure 6:
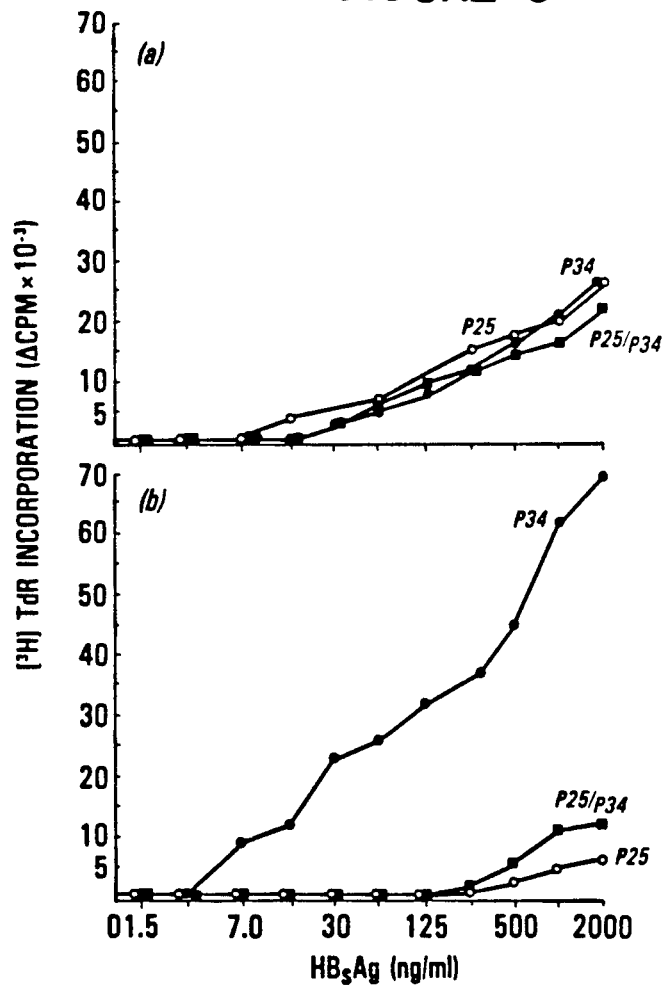

FIG. 6 contains two graphs that illustrate T cell proliferative responses induced by HBsAg/P25, and HBsAg/P34 priming. $C_3$H.Q. Mice were immunized in the hind footpads with either 16 ug of HBsAg/P25 in CFA graph (a) or 4 ug of HBsAg/P34 in CFA graph (b). Eight days following immunization, popliteal lymph node (PLN) cells were harvested and co-cultured with varying concentrations of HBsAg/P34(●), HBsAg/P25(0), HBsAg/P25/P34(■) or media alone for 4 days. Proliferation was determined by incorporation of [$^3$H]-TdR into DNA, and expressed as counts per minute (CPM) adjusted for background (ΔCPM).

Figure 7:
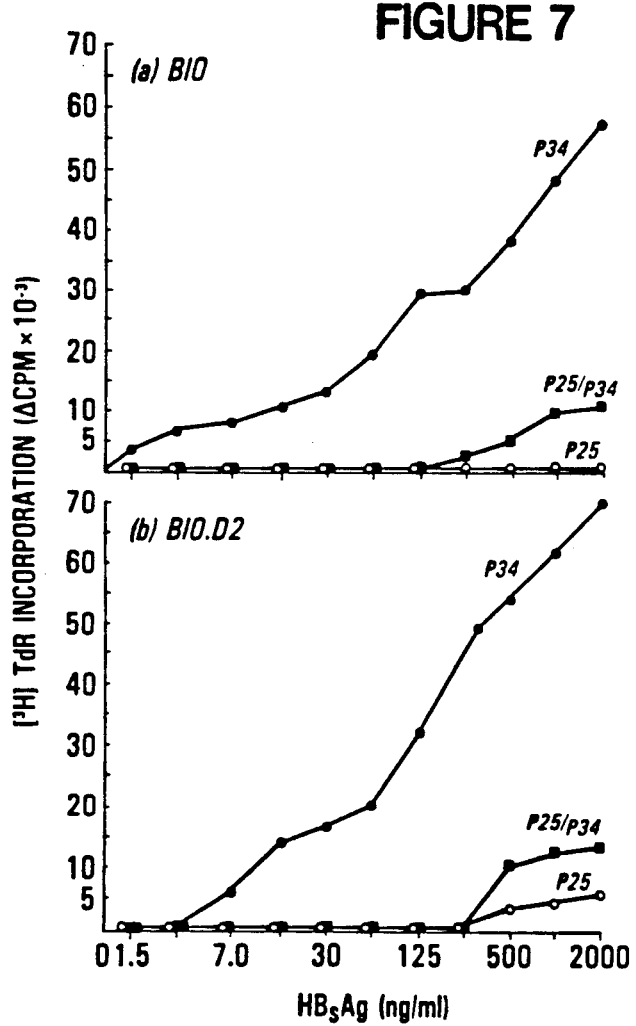

FIG. 7 contains two graphs that illustrate comparative S region-specific and pre-S(2) region-specific T cell proliferative responses. H-2 Congenic, B10 mice (graph a) and B10.D2 mice (graph b) were immunized with 4 ug of HBsAg/P34 in CFA. Eight days following immunization, PLN cells were harvested and co-cultured with the indicated HBsAg preparations, [P34(●), P25/P34 (■), P25 (0) or media alone for 4 days, as in FIG. 6. Proliferation was determined by incorporation of [$^3$H]-TdR into DNA, and expressed as CPM adjusted for background (ΔCPM).

Figure 8:
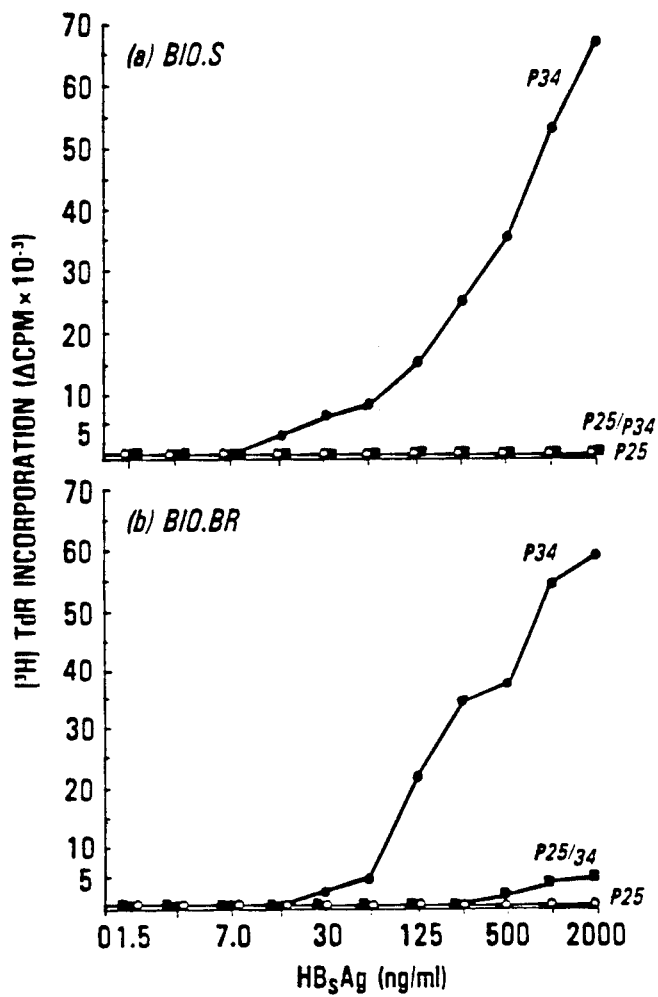

FIG. 8 contains two graphs that illustrate comparative S region-specific and pre-S(2) region-specific T cell proliferative responses. H-2 Congenic, B10.S mice (graph a) and B10.BR mice (graph b) were immunized and T cell proliferative responses determined and indicated as described in FIG. 7.

Figure 9:
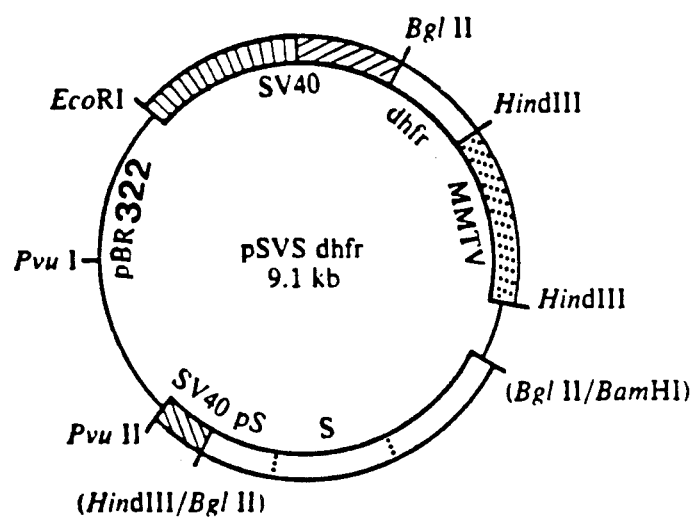

FIG. 9 is a schematic representation of plasmid pSVS dhfr as described by Michel et al., *Proc. Natl. Acad. Sci. USA*, 81, 7708 (1984).

The present invention provides several benefits and advantages.

One benefit of the invention is that it provides a means for assaying antibodies directed to a conformation-independent antigenic determinant utilizing a single polypeptide antigen that contains the amino acid residue sequences of both a conformation-dependent and a conformation-independent antigenic determinant.

Another benefit of this invention is that antibodies directed to a conformation-independent antigenic determinant may be assayed in the presence of antibodies directed to a conformation-dependent antigenic determinant where both determinants are both present in the same proteinaceous material.

A particular advantage of the invention is the demonstration of the latter assay technique for the clinically important and scientifically interesting S and pre-S(2) antigenic determinants.

Still further benefits and advantages of the present invention will be apparent to those skilled in the art from the detailed description of the invention and the specific embodiments that follow.

DETAILED DESCRIPTION OF THE INVENTION

I. Definitions

Before describing the invention in greater detail, several of the words and phrases utilized herein are defined.

Antibody—a receptor molecule produced by B cells that immunoreacts with and binds to an antigen ligand to form an immunoreactant.

Antigen—a ligand molecule that immunoreacts with and is bound by an antibody to form an immunoreactant; frequently, the immunogen to which the antibody was raised.

Antigenic determinant (determinant)—the region of a molecule containing the antigen with which the antibody forms an immunoreactant.

Epitope—specific portion of the antigenic determinant with which the antibody reacts; also referred to as an immunodominant portion of the determinant.

Amino acid residue sequence—a specifically ordered arrangement of amino acid residues linked together by peptide bonds.

Proteinaceous antigen—a relatively high molecular weight, e.g., greater than about 10 kilodaltons (kD), amino acid residue sequence that may be a single protein, a protein-peptide fusion product, a protein-like entity that lacks from its sequence one or more amino acid residues present in a protein, and the like.

Polypeptide antigen—an antigen of this invention prepared from a proteinaceous antigen.

Peptide or polypeptide—used interchangeably for a relatively low molecular weight; i.e., about 210 dalton to about 10 kD amino acid residue sequence.

Conformation-independent antigenic determinant—an antigenic determinant whose immunoreaction with and binding by an antibody depends primarily on its amino acid residue sequence, and to a minor extent, if at all, on its three-dimensional, tertiary structure. Such determinants are thus relatively linear. These determinants are also sometimes referred to as sequential, as are their epitopes.

Conformation-dependent antigenic determinant—an antigenic determinant whose immunoreaction with and binding by an antibody depends on both its amino acid residue sequence and its three-dimensional, tertiary structure; i.e., an antigenic determinant whose immunoreaction with and binding by an antibody may be substantially destroyed by change in its three-dimensional, tertiary structure such as by denaturization. Such determinants are thus relatively non-linear and typically are associated with one or more cystine disulfide bonds that form "loop" structures. These determinants are also sometimes referred to as non-sequential, as are their epitopes.

II. The Invention

A. General Discussion

The present invention contemplates a polypeptide conformation-independent antigenic determinant encoded by a genome that encodes that antigenic determinant as well as a conformation-dependent antigenic determinant. Methods of preparing the polypeptide antigen and of its use are also contemplated as is a diagnostic system that utilizes the polypeptide antigen affixed to a solid matrix as a solid support.

The present invention is described herein for diagnostic methods that utilize one specific antigen whose sequence is encoded by the hepatitis B virus (HBV) genome. However, it is believed that the embodiments described in relation to the particular exemplary polypeptide antigen are general, and are applicable to substantially any diagnostic method utilzing a polypeptide antigen prepared from a single proteinaceous antigen that includes a conformation-independent antigenic determinant and a conformation-dependent antigenic determinant.

The present invention utilizes the before-described HBsAg/P34 particles that are produced by tranfected CHO cells as described by Michel et al., *Pro. Natl. Acad. Sci. USA*, 81, 7708 (1985) as a proteinaceous antigen. The particles used in this work were provided by Michel et al. and may be prepared as described in detail by Michel et al., above. Briefly, however, those particles were reported to be prepared as follows.

A plasmid designated pSVS dhfr was constructed and used to transfect Chinese hamster ovary (CHO) cells that did not produce dihydrofolate reductase (DHFR$^-$) The PSVS dhfr plasmid was derived from plasmid pSVH$_4$ reported by Malpiece et al., *Nucleic Acids Res.*, 11, 4645 (1983), and included two transcription units in tandem arrangement.

The first transcription unit consists of the HBV 2.3 kilobase (kb) Bgl II A DNA fragment, including the pre-S(2) region, the S gene, and the HBsAg mRNA polyadenylation site, placed downstream from the simian virus 40 (SV40) early promoter. The second unit consists of murine DHRF cDNA placed under the control of the MMTV-LTR promoter, the SV40 t-antigen splice site and the SV40 early mRNA polyadenylation site. See Lee et al., *Nature (London)*, 294, 228 (1981).

More specifically, as shown schematically in FIG. 9, plasmid pSVS dhfr itself consists of the following: The SV40 DNA preceding the HBV segments corresponds to the 360-base pair Pvu II/Hind III fragment carrying the early promoter, which was fused to the 2.3 kb Bgl II-A fragment from HBV DNA by blunt-end ligation at the Hind III site. The MMTV and SV40 sequences flanking the DHFR cDNA are those present in pMTV dfhr, Lee et al., above. The pBR322 sequences correspond to the EcoRI/Pvu II fragment carrying the beta-lactamase gene and the origin of replication, and to the CHO DHFR$^-$ cells were transfected by pSVS dhfr, DHFR$^+$ cells were selected, and HBsAg was assayed for in the cell supernatants using radioimmunoassay (AUSRIA II, Abbott Laboratories, North Chicago, Ill.). Clones producing HBsAg were chosen for gene amplification, and resistant methotrexate-cells were selected. One clone designated 37BA5R50 was chosen for further study.

The CHO DHFR$^-$ cells transfected with plasmid SVS dhfr produced particles having a diameter of about 22 nanometers (nm) that had the same diameters and density in cesium chloride as the HBsAg particles found in human serum. The particles contained three proteinaceous materials having molecular weights of about 22, 26 and 34 kD, respectively. The two lighter molecular weight proteinaceous materials were reported to be two forms of the region encoded by the S gene, while the 34 kD material was reported to be encoded by both the S region and part of pre-S region genes. The particles are referred to herein as HBsAg/P34 because of the presence of the 34 kD material.

Michel et al. also reported that the particles produced by their transfected CHO DHFR$^-$ cells contained a receptor for polymerized human serum albumin (pHSA), and could be utilized to induce production of antibodies to that receptor site in mice. The present inventors, using those particles, have characterized the immunogenicity of the pre-S(2) region of those particles as is discussed herein in regard to the early appearance; i.e., appearance at an early time after immunization, of antibodies directed to the amino-terminal 26 residues of the pre-S(2) region, and have also found the use of those particles to prepare the polypeptide antigen [HBsAg/P34(SDS/2ME)]described hereinafter.

The HBsAg/P34 particles that contain the amino acid residue sequence and epitope of a conformation-independent antigenic determinant [pre-S(2) region]and the amino acid residue sequence and epitope of a conformation-dependent antigenic determinant (S region) are not required proteinaceous antigens for the invention described herein, but are exemplary of other entities that may be used to illustrate its embodiments. For assays for detecting the presence of antibodies directed to the HBV pre-S(2) regions or pre-S(2) antigenic epitopes, at least three other materials may be used as the proteinaceous antigen. Each of those materials, like the HBsAg/P34 particles, contains a plurality of antigenic protein molecules as structural subunits.

One such material is the rod-shaped particles that are referred to as HBsAg-positive filaments as discussed by Zuckerman in *Hepatitis and Blood Transfusion*, G. N. Vyas et al. eds., Grune & Stratton, New York, Chapter 30 (1973), and in the references cited therein. The described filaments are reported to have diameters of about 20 nanometers (nm) and to vary in length from less than 50 nm to 230 nm. Those filaments are non-infectious and contain expressed S and pre-S(2) regions at the same levels as do the infectious HBV entities known as Dane particles.

Dane particles are reported to be multilayered spheres, and to have an average diameter of 42 nm. Dane particles may be used herein, but are not prefered because they are highly infectious.

The third entity useful herein for work with antibodies directed to HBV encoded S and pre-S(2) regions are the spherical particles that have an average diameter of about 22 nm that are found in the blood and serum of patients who have an HBV infection. The 22 nm particles are not themselves infectious, but exhibit a lower amount of expressed pre-S(2) region relative to expressed S region than do Dane particles, the before-described CHO-derived HBsAg/P34 particles or the HBsAg-positive filaments.

Additional proteinaceous antigens that contain conformation-independent and conformation dependent antigenic determinants are known, and may be found by reference to work published utilizing synthetic or cleavage-produced polypeptides as immunogens to raise antibodies directed to three-dimensional determinants of protein molecules. For example, the work of Arnon et al., *Proc. Natl. Acad. Sci. USA*, 62, 163 (1968) indicated that the so-called "lysosyme loop" is a conformation-dependent antigenic determinant.

More recently, Green et al., *Cell*, 28, 477 (1982) reported the synthesis of linear polypeptides whose sequences covered the majority of the hemagglutinin molecule (HA1) of influenza virus X47. Those workers utilized the synthetic polypeptides to induce antibody production. They reported good binding of the antibodies directed to the carboxy-terminal region of HA1 that is relatively linear and free from conformational restraints, based on X-ray analysis, but poor binding of the anti-polypeptide antibodies to a more conformationally constrained "loop" region of HA1 located at positions 135–149 from the aminoterminus. It may be concluded from that report that the loop region constitutes a conformation-dependent antigenic determinant, while the carboxy-terminal region constitutes a conformation-independent antigenic determinant.

The epitope of the conformation-dependent antigenic determinant of the proteinaceous antigen is lacking (absent) in the polypeptide antigen while the originally present amino acid residue sequences of the conformation-dependent and conformation independent determinants are present, as is the epitope of the conformation-independent epitope. The polypeptide antigen is conveniently prepared by denaturation of the conformation-dependent epitope.

It is noted that the presence of conformation-dependent determinants and epitopes are usually identified by their reactions with antibodies. However, such regions may also be indentified by changes in nuclear magnetic reasonance or X-ray spectra of the proteinaceous antigen and polypeptide antigen before and after denaturation, respectively. In addition, denatured proteinaceous materials may be distinguished from non-denatured, native materials on the basis of differences in mobility in gel electrophoresis, circular dichroism spectra, and isoelectric points. Still further, the denatured materials contain fewer cystine disulfide bonds, and more cysteine residues (or alkylated cysteine residues) than do native materials.

Methods for denaturing proteins are well known in the art. Such denaturation may include physical effects in which the three-dimensional structure of the epitope is altered by the breaking of hydrogen and ionic bonds, as well as by chemical effects in which covalent bonds are broken. In preferred practice, both physical and chemical denaturation are utilized to prepare the polypeptide-containing antigen.

The proteinaceous antigens typically useful herein contain cystine disulfide bonds that assist in providing conformation (tertiary structure) to the epitope of the conformation-dependent antigenic determinant. As a consequence of the presence of one or more cystine disulfide bonds contributing to epitopic conformation, the denaturing agent includes a water-soluble cystine-disulfide bond-breaking agent as a chemical denaturant.

Water-soluble disulfide bond-breaking agents are well known in the chemical and biochemical arts. Those agents are typically considered to be reducing agents and include alkali metal borohydrides and cyanoborohydrides such as sodium borohydride and sodium cyanoborohydride.

Thiol-containing agents are also useful. This group of denaturing agents include reagents that are electrically neutral at a pH value of 7 and those that bear an ionic charge at that pH value. Included among the electrically neutral reagents are 2-mercaptoethanol, glycerol mono-thioglycolate, dithiothreitol, dithioerythritol and the like. Exemplary thiol-containing agents that bear an ionic charge at a pH value of 7 include 2-mercaptoethylamine, mercaptoacetic (thioglycolic) acid, 3-thiopropropionic acid and thiolactic acid, as well as the alkali metal, 2-hydroxyalkylammonium, and ammonium salts of those acids such a sodium thioglycolate, ammonium 3-thiopropionate, potassium thiolactate, di-isopropanolammonium thioglycolate, ethanolammonium thiolactate and the like.

Alkali metal and ammonium bisulfite and thiosulfate salts are also useful for breaking cystine disulfide bonds. Exemplary of such materials are sodium bisulfite, ammonium bisulfite, potassium thiosulfate, sodium thiosulfate and the like.

A water-soluble cystine disulfide bond-breaking agent that is electrically neutral at a pH value of 7 such as 2-mercaptoethanol (2ME) is particularly preferred. 2ME is used hereinafter used as an illustrative water-soluble disulfide bond-breaking agent.

It is noted that the cystine disulfide bond-breaking agents described above do not cleave peptide bonds under the normal conditions of temperature, reaction time and solvent (aqueous medium) employed in usual protein- or polypeptide-related chemistry. Consequently, the amino acid residue sequences of both conformation-dependent and -independent determinants are left present and intact after the protein antigen is reacted with the disulfide bond-breaking agent.

A physical denaturant that disrupts hydrogen bonding and/or inter-residue ionic bonding is also preferably a part of the denaturing agent. Relatively small molecules such as urea and guanidine are known to be useful for disrupting hydrogen and ionic bonds. However, it is preferred to use a relatively larger, surfactant molecule that also provides solubilization of the proteinaceous material and polypeptide.

Exemplary surfactants include anionic and nonionic materials. The anionic surfactants preferably contain a sulfate or sulfonate group as the anionic portion of the molecule and a fatty chain of 10–18 carbon atoms ($C_{10}$–$C_{18}$). Nonionic surfactants preferably include a fatty $C_{10}$–$C_{18}$ chain plus 1–100 polymerized ethylene oxide units or about 6–75 polymerized ethylene oxide units and no fatty chain.

Illustrative, useful anionic surfactants that contain a sulfate group include sodium dodecyl sulfate (SDS), ammonium lauryl sulfate (ALS), potassium lauryl sulfate, sodium decyl sulfate, sodium myristyl sulfate, sodium tallow sulfate (a mixture of sulfated alcohols derived from tallow); the alkali metal and ammonium polyethylene glycol ether sulfates of $C_{11}$–$C_{15}$ alcohols such as the sodium salt of a sulfated polyethylene glycol ether of a mixture of $C_{11}$–$C_{15}$ fatty alcohols having an average of 1–4 polymerized ethylene oxide units per molecule, the sodium salt of a sulfated polyethylene glycol ether of a mixture of $C_{12}$–$C_{13}$ fatty alcohols having an average of 1–4 polymerized ethylene oxide units per molecule, and the potassium salt of sulfated ethoxylated myristyl alcohol that contains an average of 1–4 polymerized ethylene oxide units per molecule; the ammonium and alkali metal salts of ethoxylated alkylphenols such as ammonium, sodium or potassium nonylphenyl ether sulfate in which the ether moiety contains an average of 1 reacted ethylene oxide unit per molecule, and the like.

Illustrative anionic surfactants that contain a sulfonate group include the alkali metal and ammonium salts of $C_{10}$–$C_{18}$ fatty acid isethionates such as sodium cocoyl isethionate (the sodium salt of the coconut fatty acid ester of isethionic acid), ammonium lauroyl isethionate, sodium oleoyl isethionate, potassium N-cocoyl-N-methyl taurate (potassium salt of the coconut fatty acid amide of N-methyl taurine), mixed sodium $C_{14}$–$C_{16}$ olefin sulfonates, sodium dodecylbenzenesulfonate, potassium decylbenzenesulfonate, and the like.

Useful nonionic surfactants typically include an average of one to about 100 reacted ethylene oxide units per molecule. Exemplary of such molecules are the ethoxylated $C_{10}$–$C_{18}$ fatty alcohols such as the polyethylene glycol ethers of stearyl alcohol that may contain an average of about 2,4,6,7,10,11,13,15,20,27,30,40,50 or 100 reacted ethylene oxide units per molecule; the mixed $C_{11}$–$C_{15}$ fatty alcohols that may contain an average of 5,7,9,12,20,30 or 40 reacted ethylene oxide units per molecule; the polyethylene glycol ethers of cetyl alcohol that may contain an average of 1,2,4,5,6,10,12,16,20,25,30 or 45 reacted ethylene oxide units per molecule; the ethoxylated octylphenyl ethers that may include an average of 1,3,5,7,9,10,13 or 40 reacted ethylene oxide units per molecule; the ethoxylated nonylphenyl ethers that may contain an average of 1,2,4,5,6,7,8,9,10,11,12,13,14,15,18,20, 23,30,40,50 or 100 reacted ethylene oxide units per molecule; polyethylene oxides (polyethylene glycols) that may contain an average of 6,8,9,10,12,14,16,18, 20,32,40 or 75 polymerized, reacted ethylene oxide units per molecule, and the like.

The denaturing agent is preferably used as a mixture of the surfactant and cystine disulfide bond-breaking agent. An effective amount of the denaturing agent to denature the conformation-dependent determinant and eliminate its epitope, while maintaining amino acid residue sequence of that determinant and epitope is admixed with the protein antigen. The amounts of each ingredient present in the aqueous medium utilized to denature the conformation-dependent determinant is a function of the particular reagents used as well as of the identity and amount of proteinaceous antigen used.

The determination of specific, effective amounts of denaturing agent for a given amount of protein antigen is well within the skill of those in the biochemical arts. Typically, however, the surfactant is present at about 0.1 to about 10, and more preferably at about 1 to about 5, weight percent and the disulfide bond-breaking agent is present at about 0.1 to about 10, and more preferably at about 1 to about 5, weight percent of an aqueous denaturing composition, with a protein antigen concentration from about one nanogram to about 10 milligram (mg) quantities per milliliter (ml) of aqueous denaturing medium. The HBsAg/P34 particles were denatured at a concentration of about 0.03 mg/ml.

The above-discussed admixture of an effective amount of denaturing agent and protein antigen is maintained for a predetermined period of time sufficient to denature the epitope of that determinant, and to form a previously described polypeptide antigen. The exact length of time required for that denaturization is again a parameter that can be readily determined by those skilled in the art. However, a reaction time at 37° C. of about 1 to about 5 hours is normally sufficient.

The desired polypeptide antigen is thereafter recovered by conventional means and is dried. That recovery may be by purification as by column chromatography, followed by lyophilization. More preferably, the polypeptide antigen is recovered affixed to a solid matrix such as a well of a polystyrene or polyvinylchloride microtiter plate, followed by drying in the air or in an oven.

It is particularly preferred to recover the polypeptide antigen in dry form affixed to a solid matrix. The reason for that preference is that the broken disulfide bond of a solubilized antigen may re-oxidize to reform the previously broken cystine disulfide bond, and thereby reform the original epitope. In addition, even where the cysteine mercaptan groups formed by cystine bond reduction are blocked from re-oxidation by alkylation as with iodoacetamide, an epitope substantially similar to that originally present can reform in aqueous solution. Thus, affixation to a solid matrix and drying are used to substantially permanently denature the epitope of the conformation-dependent determinant.

The desired polypeptide antigen is particularly useful affixed to a solid matrix as a solid support in solid phase immunoassays.

The antigen is typically affixed to the solid matrix by adsorption of the antigen from an aqueous medium, although several modes of affixation well known to those skilled in the art may be used. Exemplary of such modes are the reaction of the polypeptide with the reactive carboxyl functionality produced by the reaction of cyanogen bromide with glucose-containing matrices such as cross-linked dextrans or cellulosics, glutaraldehyde linking as discussed hereinafter in conjunction with latex particles, and the like.

One exemplary solid phase immunoassay is for the presence of antibodies directed to the epitope of a conformation-independent antigenic determinant such as the pre-S(2) region encoded by the HBV genome. This is shown in the graphs of FIGS. 1 and 2 and in the discussion of Section II B relating to those Figures. The solid support is also useful for solid phase immunoassays for the presence of an antigenic epitope that immunoreacts with and is bound by antibodies that also immunoreact with and bind to a conformation-independent antigenic determinant such as the pre-S(2) epitope. This is shown in FIG. 5 and in the discussion of Section II B relating to that Figure.

Useful solid matrices are well known in the art. Such materials include the cross-linked dextran available under the trademark SEPHADEX from Pharmacia Fine Chemicals (Piscataway, N.J.), agarose, beads of glass, polyvinyl chloride, polystyrene, cross-linked acrylamide, nitrocellulose or nylon-based webs such as sheets or strips, or the wells of a microtiter plate such as those made from polystyrene or polyvinylchloride.

Latex particles useful in agglutination-type assays are also useful solid matrices. Such materials are supplied by the Japan Synthetic Rubber Company of Tokyo, Japan, and are described as carboxy-functional particles dispersed in an anionic soap. Typical lots of such particles have an average diameter of 0.308 microns, and may have an average carboxy-functional group distribution of about 15 to about 30 square Angstroms per carboxy group.

Prior to use, the particles are reacted with a diamine such as 1,3-diamino-2-propanol to form a plurality of amide bonds with the particle carboxy groups while maintaining free amine groups. The free amines are thereafter reacted with a dialdehyde such as glutaraldehyde and the polypeptide antigen to form Shiff base reaction products. The Shiff base reaction products are thereafter reduced with a water-soluble reductant such as sodium borohydride to provide a useful solid support.

Those skilled in the art will understand that there are numerous methods for solid phase immunoassays that may be utilized herein. Exemplary, useful solid phase assays include enzyme-linked immunosorbant assays (ELISA), radio-immune assays (RIA) and fluorescence immune assays (FIA). Each of those assay methods may employ single or double antibody techniques in which an indicating means is utilized to signal the immunoreaction, and thereby the binding of an assayed antibody with the polypeptide antigen of the solid support. Exemplary techniques may be found explained in Maggio, *Enzyme Immunoassay*, CRC Press, Cleveland, Ohio (1981); and in Goldman, *Flourescent Antibody Methods*, Academic Press, New York, N.Y. (1980). Radioimmune assays were utilized in the study discussed in the Results section (II B) hereinafter, and will be utilized as illustrative in the discussion below.

Broadly, a solid phase immunoassay of the present invention for antibody detection includes the following steps:

(a) A solid support is provided that comprises an effective amount of a polypeptide antigen of this invention affixed to a solid matrix. As noted previously, the polypeptide antigen is a single molecule that contains (i) the amino acid residue sequence and epitope of a conformation-independent antigenic determinant such as the pre-S(2) region encoded by HBV, and (ii) the amino acid residue sequence of a conformation-dependent antigenic determinant, but lacks the epitope of that determinant.

(b) A liquid sample to be assayed is admixed with the solid support to form a solid/liquid phase admixture. The sample utilized is to be assayed for the presence of antibodies directed to the conformation-independent antigenic determinant such as antibodies directed to the pre-S(2) region encoded by HBV.

(c) The solid/liquid admixture so formed is maintained for a predetermined period of time sufficient for antibodies directed to the conformation-independent determinant to immunoreact with and bind to (form an immunoreactant with) the antigenic determinant of the solid support.

(d) The solid and liquid phases are then separated. Preferably, the solid phase is thereafter rinsed to help assure the absence thereon of antibodies that are not specifically bound to the conformation-independent determinant.

(e) The presence of antibodies bound; i.e., specifically bound, to the solid support is then determined. The presence of the bound antibodies is typically determined by means of an signal-linked second antibody indicating means directed to the Fc portion of the assayed antibodies such as where the signal is provided by gamma radiation provided by iodine-125 bonded to those antibodies. The signal means indicates the binding of the second antibodies to the first-named, assayed antibodies directed to the conformation-independent determinant, and thereby signals the presence and amount of those first-named antibodies.

The steps for a solid phase immunoassay of the present invention for the presence of an antigenic epitope are similar to those described above. However, the liquid sample to be assayed of step (b) is admixed with a predetermined amount of known antibodies that immunoreact with and bind to the epitope of the conformation-independent determinant to form a liquid, known antibody/sample, admixture. That admixture is typically carried out prior to admixture of the liquid sample with the solid support. The liquid admixture is maintained for a period of time sufficient for the known antibodies to immunoreact with and bind to the antigenic epitope present in the sample.

The liquid, known antibody/sample, admixture is then admixed with the solid support to form a solid/liquid phase admixture analogous to that formed in step (b) above. Thereafter, manipulations analogous to steps (c), (d) and (e) for the antibody-detecting method are followed. A difference in the amount of specifically bound antibodies determined in the step analogous to step (e), above, from a control amount of binding exhibited by the known antibodies indicates the presence of the antigenic epitope in the sample assayed. The determination of the control amount of antibodies bound thus constitutes a separate step in the method, and may be carried out before the determination analogous to that of step (e).

The known antibodies that immunoreact with and bind to the epitope of the conformation-independent determinant may be provided by immunization with a peptide corresponding in amino acid residue sequence to the sequence of an epitope of the conformation-independent determinant such as the 26 residue peptide corresponding to the amino-terminus of the pre-S(2) region as used herein and described by Neurath et al., *Science*, 224, 392 (1984). Additionally, anti-pre-S(2) region-containing but anti-S region-free 10-day antisera induced by HBsAg/P34 as described in relation to FIG. 1 may also be utilized.

More specifically, as already noted, an RIA was utilized in the present study to assay for the presence of antibodies directed to the conformation-independent antigenic determinant and epitope(s) of the pre-S(2) region encoded by the HBV genome. In some instances, the anti-pre-S(2) antibodies were assayed in the presence of anti-S antibodies, which would be the usual circumstance in a clinical assay involving humans. In other instances, the anti-pre-S(2) antibodies were assayed in a sample that was free from anti-S antibodies; i.e., where the amino-terminal 26 amino acid residue pre-S(2) peptide was used as immunogen, or during early stages of tne primary immune response to an immunogen containing both regions (HBsAg/P34 particle), at which time anti-S antibodies were not present in detectable quantities.

The solid support used as the solid phase in the exemplary immunoassay utilized a solid matrix of polystyrene, removable flat-bottomed microtiter wells (REMOVAWELLS available from Dynatech Lab, Alexandria, Va.). HBsAg/P34 particles, discussed before, denatured in an aqueous medium containing 2 percent 2ME and 2 percent SDS were used as the polypeptide antigen and are designated hereinafter as "HBsAg/P34(SDS/2ME)" to distinguish the particles of this invention from the precursor, proteinaceous antigen particles. The HBsAG/P34(SDS/2ME) particles were affixed to the matrix by depositing 50 microliters (ul) of a 2.5 ug/ml HBsAg/P34(SDS/2ME) aqueous solution in 0.01 molar (M) bicarbonate buffer at pH 9.6 into the well bottoms, and permitting the water to evaporate at room temperature over a period of about 18 hours (overnight).

An aqueous solution containing 1 weight percent bovine serum albumin (BSA) in phosphate-buffered saline (PBS) at pH 7.2 was then used to wash the wells. That wash step blocked non-specific binding sites on the wells (quenched the wells). The wells were rinsed with 50 ul of 10% by volume normal human serum (NHS) in PBS containing 1% BSA (PBS/NHS/BSA) prior to use.

For the assays, 50 ul of sample to be assayed (mouse serum) in titrated dilutions dissolved in PBS/NHS/BSA were admixed into the individual wells of the plates to form solid/liquid admixtures. Those admixtures W ⓔr ⓡmaintained (incubated) for a predetermined time period (2 hours at 37° C.) sufficient for anti-pre-S(2) antibodies to bind to the solid matrix-affixed polypeptide antigen. The solid/liquid admixtures were then separated, and the separated solid phases were washed with aqueous solutions of 1% BSA in PBS.

Thereafter, the presence and amount of anti-pre-S(2) antibodies bound to the solid support were determined. This determination was made by admixture of 50 ul of suitably diluted (1/300 to 1/500) goat anti-mouse IgG or IgM antisera (Meloy Laboratories, Springfield, Va.); i.e., a second antibody that immunoreacts with and binds to the mouse anti-pre-S(2) antibodies bound to the solid support, to form a second solid/liquid phase admixture. That second solid/liquid phase admixture was maintained for a second, predetermined period of time (90 minutes at 37° C.) for the second antibodies to immunoreact with and bind to the first-named [(mouse anti-pre-S(2)] antibodies. The solid and liquid phases were separated and the solid suport was rinsed to remove non-specifically bound antibodies.

Affinity-purified swine anti-goat IgG (SAGG) was purchased from Boehringer Mannheim Biochemical (Indianapolis, Ind.). The SAGG were radiolabelled with $^{125}I$ using the modification of the chloramine-T method described by McConahey and Dixon, *Int. Arch. Allergy Appl. Immunol.*, 29, 185 (1966).

50 Microliter solutions of $^{125}I$-SAGG [(third antibody; and signal means-linked second antibody of step (e), before, used as the indicating means)] containing 3.0 to $3.5 \times 10^4$ counts per minute (CPM) were added to the wells to form a third solid/liquid phase admixture. That admixture was maintained for a predetermined time (2 hours at 37° C.) sufficient for the third antibody to immunoreact with and bind to the second antibodies. The solid and liquid phases were separated. The solid phases (wells) were rinsed to remove non-specifically bound antibodies, and were placed into an automatic gamma ray counter and counted.

The highest serum dilution yielding 2.5 times the counts exhibited by preimmunization serum was considered the titer for each serum. Those titers are expressed as the reciprocal of $log_2$.

It will be apparent to those skilled in the art that the third, swine anti-goat, antibodies used in the results discussed before and hereinafter need not always be used. Use of $I^{125}$-labelled goat-anti-mouse antibodies may serve as the signal. Use of third antibodies, sometimes referred to as an amplifying reagent, provides for a more sensitive assay.

For an ELISA, typically used enzymes linked to the indicating means (third antibodies, or second antibodies if an antibody amplifying reagent is not used) as a signalling means include horseradish peroxidase, alkaline phosphatase and the like. Each of those enzymes is used with a color-forming reagent or reagents (substrate) such as hydrogen peroxide and o-phenylene diamine; and p-nitrophenyl phosphate, respectively. Enzyme-linked antibodies (conjugates) of one animal raised to the antibodies of another animal such as peroxidase-linked rabbit anti-goat, goat anti-mouse and goat anti-human antibodies, as well as phosphatase-linked goat anti-human, rabbit anti-goat, and rabbit anti-mouse antibodies are commercially available from several suppliers such as Sigma Chemical Company of St. Louis, Mo.

Similar assays may also be carried out using flourochrome dyes linked to an antibody as an indicating means to signal the presence of antibodies directed to the conformation-independent determinant. The flourochrome dye is typically linked to the third antibodies (or second antibodies, as above) by means of an isothiocyanate group to form the conjugate. Exemplary flourochrome dyes include fluorescein isothiocyanate (FITC), rhodamine B isothiocyanate (RITC) and tetramethylrhodamine isothiocyanate (TRITC). Conjugates such as FITC-linked goat anti-human, rabbit anti-mouse, goat anti-mouse, goat anti-rabbit and sheep anti-mouse antibodies, as well as TRITC-linked goat anti-human antibodies are commercially available from several sources such as Sigma Chemical Company.

In addition to the RIA, ELISA and FIA techniques for determining the presence of antibodies directed to the conformation-independent determinant such as antibodies directed to the pre-S(2) region, other well known techniques are also available. In one technique, protein A of *Staphylococcus aureus* linked to a signalling means such as $^{125}I$ is utilized to determine the presence of the assayed antibodies bound to the solid support.

In another technique, biotin linked to a third antibody (or second antibody, as before) is utilized to signal the immunoreaction in conjunction with avidin that is itself linked to a signalling means such as horseradish peroxidase. Biotin-linked antibody conjugates such as biotin-linked goat anti-rabbit, goat anti-human, goat anti-mouse and rabbit anti-goat IgG's are commercially available from Polysciences, Inc. of Warrington, Pa. Avidin-FITC, avidin-RITC, avidin-peroxidase and avidin-alkaline phosphatase are also available commercially from Polysciences, Inc. for use with the biotin-linked antibody conjugates to provide the signal. Still other techniques are well known to those skilled in this art.

As noted previously, solid phase immunoassays for the presence of an antigenic epitope such as a pre-S(2) epitope that immunoreacts with and is bound by antibodies that also immunoreact with and bind to a conformation-independent antigenic determinant are similar to the above-described assays for such antibodies. The reagents discussed hereinbefore and the ELISA, FIA and other diagnostic methods are equally applicable to antigenic epitope determinations as to determining the presence of antibodies in the sample to be analyzed. Specifics for assaying for the presence of such antigenic epitopes are described in the Results section that follows, and those skilled in the art will understand how such assays are conducted.

The specific methods described hereinafter utilized mouse sera, as already noted. In clinical studies using the particularly disclosed methods and systems, samples to be assayed would be taken from animals such as chimpanzees or humans that are susceptible to HBV infection. In addition to serum, those samples may also be cerebrospinal fluid, saliva, lymph, tracheo-bronchial washings, urine, semen, tissue homogenates and of course, blood and blood plasma.

The present invention also contemplates a diagnostic system, preferably in kit form, for assaying a sample. The sample may be assayed for the presence of antibodies directed to a conformation-independent antigenic determinant, preferably also in the presence of antibodies directed to a conformation-dependent determinant, where the conformation-independent and conformation-dependent determinants are both present in a single proteinaceous antigen. The sample may also be assayed for the presence of an antigenic epitope that immunoreacts with and is bound by antibodies that immunoreact with and bind to a conformation-independent antigenic determinant, but are free from such immunoreaction with a conformation-dependent determinant, where the conformation-independent and conformation-dependent determinants are both present in a single proteinaceous material.

The system comprises: (1) at least one container that includes an effective amount of a polypeptide antigen of this invention affixed to a solid matrix as a solid support. That antigen comprises (i) the amino acid residue sequence of a conformation-dependent antigenic determinant, but lacks the epitope of that determinant, and (ii) the amino acid residue sequence and epitope of a conformation-independent antigenic determinant in a single molecule.

Preferably included in one embodiment of the system in a second container is (2) an indicating means capable of signalling the immunoreaction of antibodies from the sample to be assayed with the conformation-independent determinant. Another embodiment of the system preferably includes (2) a second container that includes a predetermined amount of known antibodies that immunoreact with and bind to an epitope of the conformation-independent determinant of the solid support and also immunoreact with and bind to an epitope of an antigen whose presence is to be assayed in a sample, and (3) a third container that includes an indicating means capable of signalling the immunoreaction of the known antibodies with the epitope of the conformation-independent determinant of the solid support.

Exemplary of the solid support of the above system is the microtiter plate utilized in the before-desribed assay method for antibodies directed to the pre-S(2) region. That solid support or a solid support prepared using any of the previously desribed matrices may be utilized in the diagnostic system.

A solid support such as the polypeptide antigen-affixed wells described before is encompassed in the container formed by the microtiter plate. However, solid supports prepared from one of the other before-described solid matrices are contemplated as being packaged in a separate container such as a plastic or glass bottle or vial or in an envelope made of plastic or paper, or the like.

The polypeptide antigen is supplied affixed to the solid matrix in an effective amount. It will be appreciated by those skilled in the art that an effective amount of antigen for carrying out different assays will differ with those assays and with the area of the solid matrix. However, the determination of an effective amount of polypeptide antigen is well within the abilities of those skilled in this art. In the specific example utilized herein, about 125 nanograms of polypeptide antigen were utilized per solid matrix well having a diameter of about 0.5 centimeters.

The preferred indicating means for either of the antibody or antigen assay embodiments is typically the previously described third (or second), signalling means-linked antibodies or *Staphylococcus aureus* protein A discussed in regard to the assay method of this invention. The signalling means is generally supplied in freeze-dried form contained in a predetermined amount in a glass or plastic bottle.

The known antibodies of the embodiment of the system for use in the assay for the presence of the antigenic epitope of the conformation-independent determinant are typically those described in regard to the before-described solid phase immunoassay methods. Those antibodies are also preferably supplied in freeze-dried form in their container.

B. Results

1. Background

Previous studies have examined quantitative and qualitative aspects of the murine humoral and cellular immune response to HBsAg, as well as the influence of at least two H-2 linked immune response (Ir) genes. [Milich and Chisari, *J. Immunol.*, 129, 320 (1982); and Milich et al., *J. Exp. Med.*, 159, 41 (1984).] HBsAg high responder (H-$2^{d,q}$), and nonresponder haplotypes (H-$2^{f,s}$) have been identified, Milich and Chisari, above.

The HBsAg used in those studies contained the P25/GP28 polypeptides but lacked the pre-S(2)-encoded larger molecular weight polypeptides, and is referred to herein as HBsAG/P25. The immune response to pre-S(2) encoded determinants of the study described herein was examined as compared to S-encoded determinants of HBsAg in terms of immunogenicity at the T and B cell levels, specificity, H-2-linked regulation, and possible overlapping regulatory mechanisms; i.e., the possible influence of T cell helper function generated to the pre-S(2) region upon the anti-S-response.

The present study utilized HBsAg particles derived from Chinese hamster ovary (CHO) cells transfected with a plasmid containing the S gene and the pre-S(2) region encoded by the HBV genome, which will be designated as HBsAg/P34. The HBsAg/P34 particles are composed of the S-encoded P25/GP28 polypeptides plus the pre-S(2) and S-encoded GP34 polypeptide. The GP34 polypeptide corresponds to HBV GP33. [Michel et al., *Proc. Natl. Acad. Sci. USA*, 81, 7708 (1985).]

A panel of H-2 congenic murine strains was immunized with HBsAg/P34, and in vivo antibody production and in vitro T cell proliferative responses specific for pre-S(2) and S region determinants were examined. The results of these studies indicate: (1) the pre-S(2)-encoded region of HBsAg is significantly more immunogenic than the S gene-encoded group and subtype-specific determinants at the T and B cell level; (2) a dominant antibody binding site (epitope) on this pre-S(2) encoded region is represented on the amino-terminal 26 amino acids of GP34; (3) the immune response to the pre-S(2)-encoded region of HBsAg is regulated by H-2-linked genes distinct from those that regulate the responses to S region determinants; and (4) immunization of an S region nonresponder, pre-S(2) region responder strain with HBsAg/P34 can circumvent nonresponsiveness and induce an S-specific as well as a pre-S(2)-specific response.

The above-discussed conclusions from the study underlying this invention were made on the basis of the findings of the sections that follow.

2. Immunization with HBsAg/P34 elicits a superior anti-pre-S(2) region as compared to anti-S region antibody response in all strains tested.

A group of 5 mice from a panel of H-2 congenic strains were immunized intraperitoneally (i.p.) with unit doses containing 1.0 micrograms (ug) each of HBsAg/P34 emulsified in 0.2 milliliters (ml) of complete Freund's adjuvant (CFA). On a weight basis this was equivalent to 0.913 ug of S region-encoded protein and 0.087 ug of pre-S(2) region-encoded polypeptide per mouse or approximately a 10-fold excess of S region-encoded protein over pre-S(2) region-encoded polypeptide.

The IgG antibody responses specific for the S region (assayed on HBsAg/P25) and the S plus pre-S(2) regions (assayed on HBsAg/P34) were determined by solid-phase radioimmune assay (RIA) at 10 and 24 days following primary immunization and 2 weeks following secondary immunization with 0.5 ug of HBsAg/P34 in incomplete Freund's adjuvant (IFA). All the strains shown in FIG. 1 produced a 10 day, IgG anti-pre-S(2) response in the absence of a S region response, even though they received a 10-fold greater dose of S region protein as compared to pre-S(2) region protein.

The responses of these strains to a 4 ug dose of HBsAg/P25 is also shown in FIG. 1 for comparison [broken line; this represents a 46-fold greater S region antigen dose as compared to the dose of pre-S(2) region protein]. The 10 day, pre-S(2) responses were also significantly greater than the S region-specific responses in each strain immunized with 4 ug of HBsAg/P25 (FIG. 1 *a,b* and *c*).

The 24 day anti-pre-S(2) responses were also significantly higher than the anti-S region responses in each strain. The strain BlO anti-pre-S(2) response was 25-fold greater than the anti-S response (FIG. 1*a*), the strain BlO.D2 anti-pre-S(2) response was 200-fold greater than the anti-S response (FIG. 1*b*), and the BlO.S(9R) strain was still nonresponsive to the S region at 24 days, yet produced a 1:1620 titer of anti-pre-S(2) at this time point (FIG. 1*c*).

The 24 day, anti-pre-S(2) responses elicited by HBsAg/P34 immunization were also variably higher than the anti-S responses following immunization with 4 ug of HBsAg/P25. The differences in magnitude between these two responses depended on the anti-S responder status, with the order being BlO.D2, BlO, and then BlO.S(9R) (FIG. 1).

Following secondary immunization (2°), the anti-pre-S(2) and anti-S region responses were either equivalent [BlO.D2=BlO.S(9R)] or the pre-S(2) response was greater (BlO, 4-fold difference) (FIG. 1 *a,b,c*). This was not surprising in the BlO.D2 strain, since immunization with HBsAg/P25 also induced a 1:40,000 titer anti-S response (FIG. 1*b*). However, the quantity of anti-S produced by the BlO.S(9R) strain following secondary immunization with HBsAg/P34 (0.5 ug-IFA) was significantly greater (80-fold) than the anti-S produced following secondary immunization with 4 ug of HBsAg/P25 (FIG. 1*c*). In view of the relatively efficient anti-pre-S(2) response in this strain, this suggested a positive influence of the pre-S(2) response on the S-specific response.

3. Immunization of an S region nonresponder strain with HBsAg/P34 can circumvent nonresponsiveness to the S region.

Immunization of the BlO.S mouse strain with HBsAg/P34 confirmed that the anti-pre-S(2) response can positively influence the anti-S region response. The BlO.S strain is a total nonresponder to S region determinants even following secondary immunization with 4 ug of HBsAg/P25 [FIG. 2*a*; Milich et al., *J. Exp. Med.*, 159, 41 (1984)].

However, the BlO.S strain produced an IgG, 24 day response to the pre-S(2) region upon immunization with HBsAg/P34 (FIG. 2*a*).

Furthermore, upon secondary immunization with HBsAg/P34 this "S region-nonresponder" strain produced an anti-S specific response (titer=1:640) as well as a secondary anti-pre-S(2) response (titer=1:5120). It is of interest that the anti-S antibody produced by the BlO.S and BlO.S(9R) strains following HBsAg/P34 immunization was subtype-specific (i.e., anti-HBsAg/y), whereas that produced by the B10 and B10.D2 strains contained both group and subtype-specific anti-S.

The B10.BR strain was a low responder to the pre-S(2) region, but nonetheless produced a superior pre-S(2) as compared to S-specific antibody response at 24 days following HBsAg/P34 immunization, as compared to the anti-S response following HBsAg/P25 (4 ug) immunization (FIG. 2b). The B10.M strain was a virtual nonresponder to both the S and pre-S(2) regions of HBsAg (FIG. 2c).

Cumulatively, these results indicate that the pre-S(2) region of HBsAg is a superior immunogen to the S region at the humoral level with respect to effective immunization dose, and magnitude and time of onset of the primary response. Furthermore, the pre-S(2) region can have a positive influence on the S region-specific response.

4. Specificity of pre-S(2) region antibody responses. Since the anti-pre-S(2) response was measured on HBsAg particles consisting of both pre-S(2) and S region determinants (HBsAg/P34), it was desirable to establish a pre-S(2) region-specific assay. It was previously reported that pre-S(2) region antigenicity was resistant to denaturation by reduction and detergent treatment. [Neurath et al., *Science,* 224, 392 (1984).] In contrast, the major group and subtype-specific S region antigenic determinants are conformation-dependent and are quite sensitive to denaturing conditions. [Vyas et al., *Science,* 178, 1300 (1972); and Dreesman et al., *J. Gen. Virol,* 19, 129 (1973).]

HBsAg/P34 particles treated with an aqueous mixture containing denaturing amounts of sodium dodecyl sulfate (SDS) and 2-mercaptoethanol (2ME), e.g., two percent of each ingredient at the final concentration, were used as a solid phase-affixed polypeptide antigen [HBsAg/P34(SDS/2ME)] to measure pre-S(2) and not S region antibody activity, with the solid support comprising the HBsAg/P34(SDS/2ME) antigen affixed to the wells of polystyrene microtiter plates as the solid matrix. The solid matrix-affixed polypeptide antigen so prepared thus contained the amino acid residue sequence and epitope of a conformation-independent determinant [pre-S(2)], and the amino acid residue sequence of a conformation-dependent antigenic determinant but lacked the epitope of that latter, conformation-dependent antigenic determinant (S).

The recently described synthetic peptide encompassing the 26 amino-terminal amino acids of the pre-S(2) region [Neurath et al., *Science,* 224, 392 (1984)] was also used as a solid-phase ligand to assay antisera produced by immunization with the HBsAg/P34 particles. The advantages of the synthetic peptide were its defined specificity, the lack of residual "denatured" S region determinants, and the fact that it was not used as the immunogen.

That polypeptide corresponded in sequence to the amino acid residues Met-120 thrugh Gly-145 of the ayw subtype as deduced from HBV DNA. The amino acid residue sequence, written from left to right and in the direction from amino-terminus to carboxy-terminus, corresponded to the formula:

MetGlnTrpAsnSerThrThrPheHisGlnThrLeuGlnAspProArgValArgGlyLeuTyrPheProAlaGlyGly.

Using the more recently adopted single letter code for amino acid residues, the above sequence may also be written:

MQWNSTTFHQTLQDPRVRGLYFPAGG.

As illustrated in FIG. 3, antisera raised to group-specific (anti-HBs/a) and subtype-specific (anti-HBs/y) determinants of the S region were reactive on HBsAg/P25 particles, but were totally unreactive on SDS/2ME-treated HBsAg/P34 particles [HBsAg/P34(SDS/2ME)] affixed to a solid matrix and with the synthetic pre-S(2) peptide. Those antisera were also reactive with native HBsAg/P34 particles. Those results indicate the absence of cross-reactivity between the S region-encoded and pre-S(2) region-encoded antigens.

A series of murine strains was immunized with HBsAg/P34, and 24 day IgG antibody responses were compared on the three solid-phase antigens shown in FIG. 3. The B10, B10.D2 and $C_3H.Q$ strains produced antibodies at 24 days specific for both anti-pre-S(2) [detected on HBsAg/P34(SDS/2ME) and the synthetic peptide] and anti-S (detected on HBsAg/P25) antigenic determinants. However, in all cases, the pre-S(2) response was significantly greater.

Also of interest in these strains was the fact that the quantity (titer) of pre-S(2) antibody detected on HBsAg/P34(SDS/2ME) was virtually equivalent (not greater than a 2-fold difference) to the pre-S(2) antibody detected on the pre-S(2) peptide.

B10.S(9R) and B10.S strains demonstrated a pre-S(2)-specific response at 24 days and no S-specific response at this time point (FIG. 3). Again, similar quantities of pre-S(2) region antibody were detected whether assayed on solid matrix-affixed HBsAg/P34(SDS/2ME) or pre-S(2) peptide.

The B10.BR and $C_3H.Q$ strains (both $H-2^k$) were unique in that after primary immunization pre-S(2)-specific antibody was detectable only on the solid matrix-affixed HBsAg/P34(SDS/2ME) particles and not on the solid matrix-affixed pre-S(2) peptide. This may represent a quantitative difference in these low responding strains since an anti-pre-S(2) peptide response was detected following secondary immunization. Alternatively, these strains may recognize a pre-S(2) epitope not represented on the synthetic peptide.

To further explore the specificity of the anti-pre-S(2) region response, competitive antibody inhibition assays were performed comparing anti-native pre-S(2) and anti-pre-S(2) peptide antisera. The anti-native pre-S(2) antiserum was produced in B10 mice immunized with HBsAg/P34, and collected 10 days postimmunization. This antiserum was pre-S(2) region specific, and contained no anti-S reactivity (FIG. 1a). Antisera to the pre-S(2) peptide were raised to the before-discussed 26-residue peptide, and were a gift of A. R. Neurath of the Lindsley F. Kimball Research Institute of The New York Blood Center, New York, N.Y.

As shown in FIG. 4a, the immunoreaction and binding between HBsAg/P34 and anti-pre-S(2) peptide (1:5000) was quantitatively inhibited with dilutions of anti-native pre-S(2) antiserum, while anti-native S region antisera had no inhibitory effect. In the reciprocal study, the reaction between HBsAg/P34 and anti-native pre-S(2) (1:500) was also quantitatively inhibited by anti-pre-S(2) peptide antiserum, and no effect was observed with an anti-S peptide antiserum (FIG. 4b).

The anti-S peptide antiserum utilized was a gift of Dr. R. A. Lerner of the Research Institute of Scripps Clinic, La Jolla, Calif., and was raised to the peptide denominated 49a of Gerin et al., *Proc. Natl. Acad. Sci. USA*, 80, 2365 (1983). Polypeptide 49a had the sequence of positions 125 through 137 from the amino-terminus of HBsAg subtype ayw. The sequence of that polypeptide, written from left to right and in the direction from amino-terminus to carboxy-terminus, is represented by the formula:

MetThrThrAlaGlnGlyThrSerMetTyrProSerCys.

The failure to achieve 100% inhibition indicates recognition of distinct epitopes by these two antisera; however, the significant competition observed suggests that anti-peptide and anti-native pre-S(2) antisera also recognize overlapping epitopes on the pre-S(2) region. Additionally, the pre-S(2) peptide demonstrated significant inhibition of an anti-native pre-S(2) antibody interaction with HBsAg/P34 although inhibition was 112-fold less efficient (on a weight basis) as compared to HBsAg/P34 (FIG. 5).

5. Regulation of in vivo anti-pre-S(2) region antibody production is H-2-linked. The quantity (FIG. 3) and kinetics (FIGS. 1,2) of in vivo anti-pre-S(2) production were shown to vary from high responder to nonresponder phenotype amongst the H-2 congenic strains examined. Based on these results, the $H-2^{b,d,q}$ haplotypes may be classified as high responders to the pre-S(2) region (10 and 24 day responses), the $H-2^s$ haplotype as intermediate (24 day response), the $H-2^k$ halotype as low (marginal 24 day response), and the $H-2^f$ haplotype as nonresponder.

As previously reported [Milich et al., *J. Exp. Med.*, 159, 41 (1984)], in vivo antibody production and T cell proliferation specific for S region determinants are regulated by H-2-linked Ir genes. However, the hierarchy of response status amongst the H-2 haplotypes to the S region differs from that observed for the pre-S(2) region. For example, the $H-2^d$ and $H-2^q$ haplotypes are high responders to the S region, whereas the $H-2^b$ haplotype is intermediate, and the $H-2^k$ haplotype possesses a low responder phenotype, but is superior to the nonresponder status of the $H-2^s$ haplotypes. The H-2 regulation of the pre-S(2) response differs in that the $H-2^b$ haplotype is at least equivalent to the $H-2^{d,q}$ haplotypes, and the $H-2^s$ haplotype is an intermediate as opposed to a nonresponder phenotype. These data indicate that distinct H-2-linked genes influence S and pre-S(2)-specific in vivo antibody production.

6. The T cell proliferative response specific for the pre-S(2) region of HBsAg is significantly greater than the T cell proliferative response specific for the S region. Several factors relative to in vivo antibody production to the pre-S(2) region of HBsAg suggested the influence of pre-S(2)-specific T cell help as opposed to T cell help derived through recognition of S region determinants; i.e., pre-S(2) as hapten. First, in vivo anti-pre-S(2) antibody production is H-2-linked in a manner distinct from anti-S antibody production (FIG. 3). Second, immunization with HBsAg/P34 induces significant amounts of anti-pre-S(2) antibody of the IgG class as early as 10 days following i.p. immunization with 0.087 ug of pre-S(2) protein, and in fact the IgG antibody titer was found to be higher than the IgM response at 10 days. Third, HBsAg/P25 nonresponder status could be circumvented by immunization with HBsAg/P34.

To directly examine T cell recognition of the pre-S(2) region of HBsAg, T cell proliferative responses of HBsAg/P34-primed mice were determined. Mice were immunized with a total of 4 ug of HBsAg/P34 or 16 ug of HBsAg/P25 in CFA in the hind footpads. Draining PLN cells were harvested at day 8 and co-cultured with various concentrations of HBsAg/P34, HBsAg/P25 or an HBsAg preparation composed primarily of HBsAg/P25 but containing a small amount of P34 as well (HBsAg/P25/P34).

These preparations were assayed for pre-S(2) antigen by quantitative inhibition of an anti-pre-S(2) antiserum (FIG. 5). HBsAg/P34 inhibited approximately 28-fold more efficiently than did HBsAg/P25/P34, based on concentrations necessary to yield 50% inhibition. The HBsAg/P25 preparation was totally nonreactive. These preparations exhibited the same pattern when tested against anti-pre-S(2) peptide antiserum.

Since those three HBsAg preparations all contained equivalent amounts of S region protein, it was expected that they would elicit comparable T cell proliferative responses in PLN T cells primed with HBsAg/P25, and this was found to be the case (FIG. 6a). $C_3H.Q$ Mice were immunized with 16 ug of HBsAg/P25 (amount required to elicit an optimal 8 day, S region-specific, T cell proliferative response) [Milich et al., *J. Immunol.*, 130, 1401 (1983)], 8 day PLN T cells were challenged with varying concentrations of the three HBsAg preparations, and the dose response curves were determined.

Immunization with HBsAg/P25-primed S region-specific T cells, which proliferated equivalently upon challenge in vitro with the various HBsAg preparations (FIG. 6a). The magnitude of S region-specific T cell proliferation and the dose response curves observed were consistent with what has previously been found in this strain. In contrast, immunization of $C_3H.Q$ mice with 4 ug of HBsAg/P34 (3.65 ug S; 0.35 ug pre-S(2)) induced a pre-S(2)-specific T cell proliferative response of significantly greater magnitude with a left-shifted dose response curve as compared to the S region-specific T cell response (FIG. 6b).

For example, an in vitro concentration of 2000 nanograms per milliter (ng/ml) of HBsAg/P25 was required to elicit a T cell proliferative response equivalent to 7.0 ng/ml of HBsAg/P34 (286-fold difference). The minimal S region-specific T cell response can be attributed to a suboptimal S region priming dose (3.65 ug). It is noted that a pre-S(2) region priming dose of 0.35 ug is 10-fold less than the S region dose and 45-fold less than an optimal S region (HBsAg/P25) priming dose of 16 ug, yet induced a significantly greater T cell proliferative response than either dose of the S region antigen (FIGS. 6 a,b). Those data indicate that the pre-S(2) region is more immunogenic than the S-encoded region of HBsAg at the T cell level in terms of the effective priming dose, the magnitude of T cell proliferation, and the quantitative in vitro dose response curve.

To confirm the T cell nature of the PLN cellular proliferation, antigen-dependent, IL-2 production was always determined in duplicate cultures. In all the 8 day PLN cultures reported herein, antigen dose-dependent, IL-2 production correlated exactly with the PLN proliferative responses as previously found for S region T cell responses. The HBsAg specificity of the proliferative responses was confirmed by the fact that the ovalbumin-primed PLN cells were not induced to proliferate or secrete Il-2 by any of the HBsAg preparations.

7. The pre-S(2)-specific T cell proliferative response is regulated by H-2-linked genes and correlates with in vivo anti-pre-S(2) antibody production. To assess both the influence of H-2-linked genes on the pre-S(2)-specific T cell proliferative response and the relevance of this response to in vivo anti-pre-S(2) antibody production, the T cell proliferative response to HBsAg/P34 in a series of H-2 congenic strains was examined. The strains studied in decreasing order of magnitude of anti-pre-S(2) antibody production were: BlO, BlO.D2, BlO.S, and then BlO.BR Since an HBsAg/P34 immunizing dose of 4 ug clearly differentiated between pre-S(2) and S-specific T cell proliferative responses in the $C_3H.Q$ strain (FIG. 6b), this dose was used throughout to prime groups of 4 mice from each strain. Draining PLN cells were harvested 8 days following immunization and were challenged in vitro with HBsAg/P34, HBsAg/P25 or HBsAg/P25/P34.

Similar to the $C_3H.Q$ strain, the BlO strain demonstrated a pre-S(2)-specific T cell proliferative response, and significant proliferation (e.g., 2000 CPM above background) was observed at a minimum HBsAg/P34 concentration as low as 1.5 ng/ml (FIG. 7a). The total absence of an S region-specific (HBsAg/P25) T cell response in this strain was noted, indicating that the minimal response induced by the HBsAg/P25/P34 antigen was pre-S(2)-specific.

The BlO.D2 strain also produced a pre-S(2)-specific T cell response, and with a minimum HBsAg/P34 dose of 7.0 ng/ml (4.7-fold difference between BlO and BlO.D2) FIG. 7b). A marginal, but positive S region-specific response in this strain is noted, as compared to the negative response of the BlO strain, which is consistent with the HBsAg/P25 responder status of these strains (BlO.D2 greater than BlO).

The S region-nonresponder, BlO.S strain also demonstrated a pre-S(2)-specific T cell proliferative response following HBsAg/P34 priming (FIG. 8a). However, the dose response curve was right-shifted relative to the BlO and BlO.D2 strains with a minimal HBsAg/P34 dose of 15 ng/ml (10-fold difference between strains BlO and BlO.S). HBsAg/P25 and HBsAg/P25/P34 did not elicit a response in this strain consistent with S region nonresponder status, and an apparent limiting amount of pre-S(2) protein, respectively.

The BlO.S strain is non-responsive at the T cell level even to an optimal 16 ug dose of HBsAg/P25. Therefore, anti-S region antibody production following HBsAg/P34 immunization in this strain most likely reflects functional pre-S(2) region-specific T cell help for S-region recognizing B cell clones. This "cross-regional" T cell help appears to be limited to S region subtype determinants, since group-specific anti-S region is not produced.

The lowest pre-S(2) responder strain in terms of antibody production is BlO.BR, which is also the lowest responder measured by T cell proliferation (FIG. 8b). The minimal HBsAb/P34 concentration to elicit a proliferative response was 30 ng/ml (20-fold difference between strains BlO and BlO.BR), and the pre-S(2) specificity was again demonstrated by the minimal to absent T cell activation by the alternate HBsAg preparations.

A difference between S region and pre-S(2) region T cell proliferative responses is that strain variation relative to the pre-S(2) region is characterized by shifts in dose-response curves with minimal differences in proliferation at maximal antigen concentrations. In contrast, S region-specific T cell proliferative responses among high to low responder strains differ in both respects. This observation suggests possible qualitative differences in T cell recognition of the pre-S(2) as opposed to the S region. Based on the in vitro T cell antigen dose response curves, the hierarchy of pre-S(2)-specific T cell responsiveness, in decreasing order from left to right, BlO, BlO.D2, BlO.S, BlO.BR correlates with in vivo anti-pre-S(2) antibody production in these H-2 congenic strains. These results indicate the H-2-linked-genes influence pre-S(2)-specific T cell proliferative responses as well as in vivo antibody production and are probably identical.

8. The pre-S(2)-induced T cell proliferative response with other immunogens. The T cell proliferative responses illustrated in FIGS. 6–8 in sections II B(6)–(7) hereinbefore were related to both the pre-S(2) and co-transcribed S regions as immunogens, and compared the S and pre-S(2) regions as T cell stimulating effectors. The T cell proliferative effects of the pre-S(2) region were the strongest ever observed by the present inventors.

Keyhole limpet hemocyanin (KLH) is a protein that is frequently utilized as a carrier for relatively low molecular weight, haptenic polypeptide conjugates used in the preparation of vaccines and other inocula. KLH is a relatively scarce protein, but it is utilized as a carrier in immunogenic polypeptide conjugates because of its general T cell stimulatory and proliferative effects.

Because of the strong T cell proliferation induced by the pre-S(2) region of HBV, it is believed that the pre-S(2) region or amino acid residue sequences within that region may be used in place of KLH to provide the T cell proliferation desired for vaccines and other inocula for inducing the production of antibodies to another immunogen.

Thus, the entire 55 residue pre-S(2) region polypeptide or another polypeptide whose sequence includes the T cell proliferating portion of the pre-S(2) polypeptide may be chemically coupled or linked to another, primary immunogen to form a conjugate. The resulting conjugate may then be incorporated into a vaccine or other inoculum as an active immunogen. In addition to the already described pre-S(2) region-containing inducer of T cell proliferation, Heermann et al., *J. Virol.*, 52, 396 (1984) and Stibbe and Gerlich, *J. Virol.*, 46, 626 (1983) have reported the production of an 11 kD polypeptide that may be used herein. That material was reported produced by cleavage of GP39 and GP42; and GP33 and GP36 polypeptides, respectively, from HBV-infected serum using the *Staphylococcus aureus* V8 enzyme. The 11 kD polypeptide was reported to contain the 55 residues of the pre-S(2) region as well as some amino-terminal residues of the amino-terminus HBV S region.

In one embodiment, the 55 residue polypeptide is used as a carrier for the primary immunogen such as a polypeptide corresponding to positions 110–137 from the amino-terminus of the HBsAg protein disclosed as peptides 49, 49a and 72 by Gerin et al., *Proc. Natl. Acad. Sci. U.S.A.*, 80, 2365 (1983), the polypeptide corresponding to positions 141–160 from the amino-terminus of the $VP_1$ protein of foot-and-mouth disease virus (FMDV) as disclosed by Bittle et al., *Nature*, 298, 30 (1982), or the like. The second immunogen may be coupled to the 55 residue carrier polypeptide by means well known in the art such as by glutaraldehyde, water-soluble carbodiimide or the like.

In another embodiment, the pre-S(2) polypeptide or the T cell proliferation-inducing portion thereof is coupled to a carrier along with the immunogen to which antibodies are desired. In this instance, a carrier such as tetanus toxoid that is amenable to human use may be employed. Coupling techniques such as those described above may also be utilized in this embodiment.

In yet another embodiment, the pre-S(2) polypeptide or its T cell-proliferating portion may be polymerized with the polypeptide immunogen against which antibodies are desired. Several means of copolymerization of polypeptides are known in the art.

In one illustrative method, cysteine (Cys) residues are provided at the amino- and carboxy-terminii of each of the polypeptides to thereby provide what may be referred to as di-Cys polypeptides. Di-Cys polypeptide of the desired immunogen such as the before-described HBsAg or FMDV polypeptides reported by Gerin et al. and Bittle et al., respectively, are admixed in an aqueous composition with an effective proportion of a di-Cys pre-S(2) region polypeptide such as a polypeptide containing the complete 55 amino acid residue sequence of the pre-S(2) region, plus terminal Cys residues. The resulting admixture is oxidized as with air until substantially no free mercaptan groups remain in the composition to prepare the co-polymer.

The resulting co-polymer-containing aqueous composition may be used as is, concentrated for use, dried as by lyophilization, or the co-polymer may be purified therefrom as by the use of gel-exclusion chromatography or the like. In typical preparations, the co-polymer is utilized in a vaccine or inoculum after purification.

In addition to augmenting the T cell response of host animals, the pre-S(2) region has been shown by the results discussed in regard to FIG. 2 to also potentiate the B cell response of otherwise poorly responding animals (low and nonresponding animals) to the production of antibodies directed to the S region. Thus, the pre-S(2) region appears to generate T cell helper activity that functions to induce S region as well as pre-S(2) region antibody production, and thereby acts to circumvent S region nonresponsiveness in inoculated animals.

The results discussed before thus indicate that an enhanced humoral immune response (potentiation) in a host animal that normally exhibits a poor or no response (low response) to an S region immunogen is provided by introducing into the animal an inoculum that contains a pre-S(2) region sequence on the same polypeptide as the S region. Those results illustrate chemical linking of the pre-S(2) region polypeptide to the primary S region immunogen by a peptide bond.

Those results also illustrate a method of potentiating the humoral immune response to an HBV S region immunogen in animals that exhibit a low humoral immune response to that immunogen. In accordance with that method, the humoral immune response of a host animal to an immunogen of the S region encoded by the hepatitis B virus genome may be enhanced by introducing into the host animal an inoculum containing a potentiating amount of a pre-S(2) region-containing polypeptide that is chemically coupled to an S region immunogen and dispersed as a unit dose in a physiologically tolerable diluent. A potentiating amount of the pre-S(2) region-containing polypeptide utilized is at least about one-twentieth the amount of the assayable amount of S region immunogen present and may be about equal to the amount of S region immunogen that is assayable.

The S region immunogen and pre-S(2) region potentiator must be present in the same molecule as was the case for the data shown in regard to FIG. 2 wherein the CHO-transfected HBsAg/P34 particles were utilized and the weight ratio of pre-S(2) region to S region immunogens was about 1:10. The S region primary immunogen and pre-S(2) region potentiator may also be separate entities, that are chemically coupled or linked together prior to use by a method such as has already been described.

For a vaccine containing an S region immunogen, that immunogen may be provided by the before-described HBsAg/P34 particles. Additional S region immunogens include the before-described HBsAg-positive filaments, the 22 nm HBsAg-containing particles found in the blood of HBV-infected animals as are usually used in vaccines against HBV, the synthetic polypeptides denominated 49, 49a and 72 reported by Gerin et al., *Proc. Natl. Acad. Sci. USA*, 80, 2365 (1983), the synthetic polypeptides reported by Dreesman et al., *Nature*, 295, 158 (1982) and the like.

The HBsAg/P34 particles may also provide the pre-S(2) region potentiator. Additional pre-S(2) region potentiators include the 11 kD polypeptides reported by Heermann et al., *J. Virol.*, 52, 396 (1984) and by Stibbe and Gerlich, *J. Virol.*, 46, 626 (1983), the HBsAg-positive filaments discussed before, a 55 residue polypeptide corresponding in sequence to the pre-S(2) region encoded by the HBV genome, and the like.

Where both the S region immunogen and pre-S(2) region potentiator are administered in a vaccine, the amount of assayable S region immunogen is the amount that is present in the vaccine and may be assayed by the antigenic epitope technique described herein, by use of a commercially available S region assay kit such as that sold under the trademark AUSRIA II by Abbott Laboratories, or by a similar assay method. The amount of pre-S(2) region polypeptide may be assayed by inhibition of a known anti-pre-S(2) region-specific antiserum as described herein.

A vaccine that includes both an S region-containing primary immunogen and a pre-S(2) region-containing potentiator contains an amount of S region immunogen effective to provide protection in an animal that exhibits a humoral immune response to an S region-containing immunogen chemically coupled to a pre-S(2) region-containing potentiator, wherein the responding animal is of the same species as the vaccinated animal that exhibits a low response to that immunogen. Effective amounts of the individual S region immunogen utilized will vary with the specific immmunogen utilized, the host animal, the rate at which a given antibody titer is desired to be obtained in the animal, the inoculation regimen utilized, and the like as are well known to a worker skilled in immunology. For the mice of the present study, the vaccines contained about 0.9 micrograms of S region-containing primary immunogen of which about 0.25 micrograms of S region-containing primary immunogen were chemically linked to the pre-S(2) region polypeptide.

Typically, unit doses of S region immunogen for host animals such as the mice used herein contain about 0.1 to about 10 micrograms of S region immunogen per animal. The mice typically weighed about 25 grams, and thus, an effective amount using the HBsAg/P34 particles as illustrative would be about 4 to about 400 micrograms per kilogram of body weight of the inoculated animal. Gerin et al., above, reported using protective unit doses of a KLH-polypeptide conjugate that contained 1 milligram of polypeptide per 0.5 milliliter dose per chimpanzee, wherein the polypeptide corresponded to positions 110–137 from the amino-terminus of HBSAg subtype ayw. Vaccines for protecting humans from HBV typically contain about 20 micrograms of the S region-containing 22 nm HBsAg particles per dose.

Physiologically tolerable diluents are well known in the vaccine and inoculum arts, and include distilled or deionized water, normal saline, phosphate-buffered saline and the like. Such diluents may also include adjuvants such as complete Freund's adjuvant, incomplete Freund's adjuvant, alum, pertussis and the like as are also well known.

The present invention has been described with respect to preferred embodiments. It will be clear to those skilled in the art that modifications and/or variations of the disclosed compositions and methods can be made without departing from the scope of the invention set forth herein.

What is claimed is:

1. A method of enhancing the humoral immune response to an S region immunogen encoded by the hepatitis B virus genome in an animal that exhibits a low response to that immunogen which method comprises introducing into said animal an effective amount of a vaccine comprising a physiologically tolerable diluent that includes dispersed therein a potentiating amount of a pre-S(2) region polypeptide encoded by said viral genome that is chemically coupled to an S region polypeptide immunogen cpable of inducing a protective response in an animal that exhibits a response to an S region-containing immunogen.

2. The method of claim 1 wherein said potentiating amount is at least about one-twentieth of the amount of assayable S region immunogen.

3. The method of claim 1 wherein said S region polypeptide immunogen includes the amino acid residue sequence of HBsAg from about position 110 to about position 137 from the amino-terminus thereof.

4. The method of claim 3 wherein S region polypeptide immunogen is the polypeptide having the amino acid residue sequency of HBsAg from about position 110 to about position 137 from the amino-terminus thereof.

5. An immunogenic conjugate comprising a T cell-stimulating polypeptide consisting essentially of 55 amino acid residues having a sequence that corresponds to the pre-S(2) region of the HBsAg GP33 glycoprotein chemically coupled to a hepatitis B S region immunogen selected from the group consisting of a HBsAg/P34 particle, a HBsAg-positive filament, a 22 nm particle and a polypeptide that includes the amino acid residue sequence of HBsAg from about position 110 to about position 137 taken from the amino-terminus thereof, said coupled 55-residue sequence constituting at least about one-twentieth the amount of the assayable S region immunogen present and being in addition to any of said 55-residue polypeptide present in said S region immunogen.

6. The immunogenic conjugate of claim 5 that comprises said T cell-stimulating polypeptide consisting essentially of 55 amino acid residues having a sequence that corresponds to the pre-S(2) region of the HBsAg GP33 glycoprotein chemically coupled to a polypeptide that corresponds to the amino acid residue sequence of the HBsAg S protein from position 110 to position 137 taken from the amino-terminus thereof.

7. A vaccine against HBV comprising an effective amount of the immunogenic conjugate of claim 5 dispersed in a physiologically tolerable diluent.

8. A method of enhancing the humoral immune response to an S region immunogen encoded by the hepatitis B virus genome in an animal that exhibits a low response to that immunogen which method comprises introducing into said animal an effective amount of a vaccine constituted by physiologically tolerable diluent that includes dispersed therein a potentiating amount of a pre-S(2) region polypeptide encoded by said viral genome that is chemically coupled to an S region immunogen capable of inducing a protective response in an animal that exhibits a response to an S region-containing immunogen, said S region immunogen being selected from the group consisting of a HBsAg/P34 particle, a HBsAg-positive filament, a 22 nm particle and a polypeptide that includes the amino acid residue sequence of HBsAg from about position 110 to about position 137 from the amino-terminus thereof, said coupled pre-S(2) region polypeptide being in addition to any of said 55-residue polypeptide present in said S region immunogen.

* * * * *

UNITED STATES PATENT AND TRADEMARK OFFICE
CERTIFICATE OF CORRECTION

PATENT NO.  : 4,683,136
DATED       : July 28, 1987
INVENTOR(S) : David Milich and Frank Chisari It is certified that error appears in the above-identified patent and that said Letters Patent is hereby corrected as shown below:

Column 5, line 33, delete "0.1M" and insert --0.01M--.

Column 8, line 21, delete "pSVH$_4$" and insert --pSVH4--.

Column 8, lines 46-47, after "to the" insert -- 346-base pair BAM HI/Hind III fragment --.

Claim 1, line 10, delete "cpable" and insert --capable--.

Signed and Sealed this

Second Day of August, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO.   :   4,683,136
DATED        :   July 28, 1987
INVENTOR(S)  :   David Milich and Frank Chisari It is certified that error appears in the above-identified patent and that said Letters Patent is hereby corrected as shown below:

Column 1, after the heading "DESCRIPTION" and before the heading "TECHNICAL FIELD", insert the following paragraph:

--This invention was made with government support under Contract AI 20720 awarded by the National Institutes of Health. The government has certain rights in the invention.--

Signed and Sealed this

Twenty-fifth Day of January, 1994

Attest:

BRUCE LEHMAN

*Attesting Officer*  *Commissioner of Patents and Trademarks*